(12) United States Patent
Archibald et al.

(10) Patent No.: US 6,548,735 B1
(45) Date of Patent: *Apr. 15, 2003

(54) PRODUCTION OF HETEROLOGOUS PROTEIN IN MILK OF TRANSGENIC NON-HUMAN MAMMALS COMPRISING A CONSTRUCT WITH AN INTRON

(75) Inventors: Alan Langskill Archibald, Edinburgh (GB); Anthony John Clark, Midlothian (GB)

(73) Assignee: PPL (Holdings) Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/781,518

(22) Filed: Jan. 9, 1997

Related U.S. Application Data

(62) Division of application No. 08/359,854, filed on Dec. 20, 1994, now Pat. No. 5,650,503, which is a continuation of application No. 07/926,192, filed on Aug. 7, 1992, now abandoned, which is a continuation of application No. 07/536,672, filed as application No. PCT/GB89/01343 on Nov. 13, 1989, now abandoned.

(30) Foreign Application Priority Data

Nov. 11, 1988 (GB) .............................................. 8826446

(51) Int. Cl.$^7$ ........................ C12P 21/00; A01K 67/027
(52) U.S. Cl. ................................. 800/7; 800/4; 800/14
(58) Field of Search ........................... 435/172.1, 172.3, 435/325, 320.1, 352, 354, 69.1; 800/2, DIG. 1, 4, 7, 14; 536/23.1, 23.4, 23.5, 23.2, 24.1; 935/9, 13, 14, 32, 24, 33, 34, 60, 63, 66

(56) References Cited

U.S. PATENT DOCUMENTS

| | | | |
|---|---|---|---|
| 4,873,316 A | * 10/1989 | Meade et al. | 530/412 |
| 5,108,909 A | 4/1992 | Haigwood | 435/69.2 |
| 5,304,489 A | * 4/1994 | Rosen | 435/320.1 |
| 5,322,775 A | 6/1994 | Clark et al. | 435/69.1 |
| 5,366,894 A | 11/1994 | Clark et al. | 435/320.1 |
| 5,439,824 A | 8/1995 | Brantly et al. | 435/320.1 |
| 5,565,362 A | 10/1996 | Rosen | 435/320.1 |

FOREIGN PATENT DOCUMENTS

| | | |
|---|---|---|
| EP | 0 264 166 | 4/1988 |
| WO | 88/00239 | * 1/1988 |
| WO | WO 88/01648 | 3/1988 |

OTHER PUBLICATIONS

Webster's II New Riverside University Dictionary (Soukhanov et al., eds.) 1984, Houghton Mifflin Company, Boston, MA p. 67.*

Houdebine et al. (1994) J. Biotechnol. 34: 269–287.*

Krimpenfort et al. Generation of Transgenic Dairy Cattle Using 'In Vitro' Embryo Production. Bio/Technology, vol. 9, pp. 844–847., Sep. 1991.*

Pursel et al. Genetic Engineering of Livestock. Science, vol. 244, pp. 1281–1288, Jun. 16, 1989.*

Anson et al., "The gene structure of human anti–haemophilic factor IX," *EMBO J.* 3(5):1053–1060 (1984).

Baker et al., in: *The Study of Biology* 4th ed. Addison–Wesley Publishing: MA, pp. 922–923 (1982).

Brinster et al., "Introns increase transcriptional efficiency in transgenic mice," *Proc. Natl. Acad. Sci. USA* 85:836–840 (1988).

Buchman et al., "Comparison of Intron–Dependent and Intron–Independent Gene Expression," *Mol. Cell. Biol.* 8(10):4395–4405 (1988).

Chandy, K.G. et al., "A family of three mouse potassium channel genes with intronless coding regions," *Science* 247:973–975 (1990).

Ciliberto et al., "Cell–Specific Expression of a Transfected Human α1–Antitrypsin Gene," *Cell* 41:531–540 (1985).

Clark et al., "Pharmaceuticals from transgenic livestock," *Tibtech* 5:20–24 (1987).

Ebert, K.M. et al., "Transgenic Production of a Variant of Human Tissue–Type Plasminogen Activator in Goat Milk: Generation of Transgenic Goats and Analysis of Expression," *Bio/Technol.* 9:835–838 (1991).

Fisher et al., "Isolation and Characterization of the Human Tissue–type Plasminogen Activator Structural Gene Including Its 5' Flanking Region," *J. Biol. Chem.* 260(20):11223–11230 (1985).

Gross et al., "Introns Are Inconsequential to Efficient Formation of Cellular Thymidine Kinase mRNA in Mouse L Cells," *Molec. Cell. Biol.* 7(12):4576–4581 (1987).

McClenaghan, M. et al., "Production of Human α1–Antitrypsin in the Milk of Transgenic Sheep and Mice: Targeting Expression of cDNA Sequences to the Mammary Gland," *Animal Biotech.* 2(2):161–176 (1991).

Simons et al., "Alteration of the quality of milk by expression of sheep β–lactoglobulin in transgenic mice," *Nature* 328:530–532 (1987).

Thilly, W.G., in: *Mammalian Cell Technology.* Butterworth's: Stoneham, MA, pp. 17–19 (1986).

(List continued on next page.)

*Primary Examiner*—Deborah Crouch
(74) *Attorney, Agent, or Firm*—Sterne, Kessler, Goldstein & Fox P.L.L.C.

(57) ABSTRACT

Proteinaceous products can be produced by transgenic animals having genetic constructs integrated into their genome. The construct comprises a 5'-flanking sequence from a mammalian milk protein gene (such as beta-lactoglobulin) and DNA coding for a heterologous protein other than the milk protein (for example a serin protease such as alpha$_1$-antitrypsin or a blood factor such as Factor VIII or IX). The protein-coding DNA comprises at least one, but not all, of the introns naturally occurring in a gene coding for the heterologous protein. The 5'-flanking sequence is sufficient to drive expression of the heterologous protein.

10 Claims, 21 Drawing Sheets

OTHER PUBLICATIONS

Van Brunt, J., "Molecular Farming: Transgenic Animals as Bioreactors," *Bio/Technol.* 6(10):1149–1154 (1988).

*Webster's II New Riverside University Dictionary*, Houghton Mifflin Co.: Boston, p. 66 (1984).

Whitelaw, C.B.A. et al., "Targeting Expression to the Mammary Gland: Intronic Sequences Can Enhance the Efficiency of Gene Expression in Transgenic Mice," *Transgenic Res.* 1:3–13 (1991).

Wilmut et al., "A revolution in animal breeding," *New Scientist* 119(1620):56–59 (1988).

Wright et al., "High Level Expression of Active Human Alpha–1–Antitrypsin in the Milk of Transgenic Sheep," *Bio/Technol.* 9:830–834 (1991).

* cited by examiner

SphI
gcatgcgcctcctgtataaggccccaagcctgctgtctcagccctcc

BLG|AAT
*->               MetProSerSer
actccctgcagagctcagaagcacgacccag|cgacaatgccgtcttct
            PvuII-0|TaqI-0

ValSerTrpGlyIleLeuLeuLeuAlaGlyLeuCysCysLeuValPro
gtctcgtggggcatcctcctgctggcaggcctgtgctgcctggtccct
           ^^^

BamHI
ValSerLeuAlaGluAspProGlnGlyAsp
gtctccctggctgaggatccccagggagat

*Sequence of AATB (pIII-I5BLGgAAT) from the SphI site
corresponding to the 5' flanking sequences of
β-lactoglobulin through the fusion to the alpha1-
antitrypsin sequences. The key restriction sites for
SphI and BamHI are underlined.*

\* = *transcription start point*
*BLG* = *β-lactoglobulin*
*AAT* = *α1-antitrypsin*
^^^ = *indicate three nucleotides missing from the
published sequence of Ciliberto, Dente & Cortese (1985)
Cell 41, 531-540, but clearly present in the clone
p8α1ppg procured from these authors. The nucleotides are
present in the published sequence of α1-antitrypsin
described by Long, Chandra, Woo, Davie & Kurachi (1984)
Biochemistry 23, 4828-4837.*

*Fig.5.*

Construction of pSS1tgXSΔClaBLG(BB)

pUCβlacA

▒ Complimentary 44-mer oligo-
   nucleotides

■ 457 bp StyI-SmaI
   fragment from β-Lg 931 pUCβlacB

▒ 163 bp SphI-StuI fragment
   from pSS1tgSE
■ insert of pUCβlacA
▒ pUC19

Construction of AATC: pSS1pUCXSAAT.TGA

Synthesis of oligonucleotides: 5' CTTGTGATATCG
3' CACTATAGCTTAA 5' } Fig. 9a.

Ligate annealed oligos into StyI/EcoRI cleaved pSS1tgSE to construct plasmid pSS1tgSE.TGA

} Fig. 9b.

Cleave with EcoRI: Blunt with Klenow polymerase. Second cleavage with SpHI. Isolate SpHI-EcoRI (blunted) fragment.

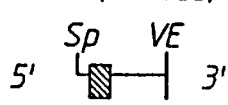

} Fig. 9c

Cleave plasmid pBJ7 (this patent) with SphI and Pvu II. Isolate large 4.3 kb) fragment. } Fig. 9d

Ligate SphI-EcoRI(blunt) fragment (3) with SphI-PvuII fragment (4) to produce pSS1tgSpX.TGA

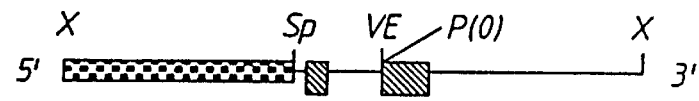

} Fig. 9e

Isolate SphI-XbaI insert from pSSItgSpX.TGA (5) and ligate to 4.2 kb SalI-SphI fragment from pSSItgXS (previous patent) and XbaI-SalI cleaved pUC18 to yield pSS1pUCXS.TGA

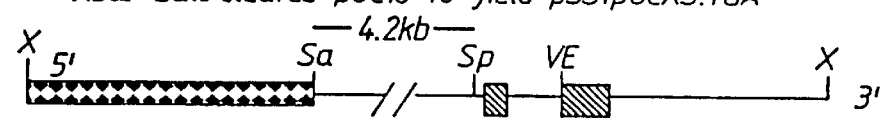

Fig. 9f

Insert AccI-HindIII AAT insert from pUC8α1AT.73 (this patent) into the unique EcoRV site of pSS1pUCXS.TGA to produce pSS1pUCXSAAT.TGA. For microinjection the XbaI-SalI fragment is excised from the vector.

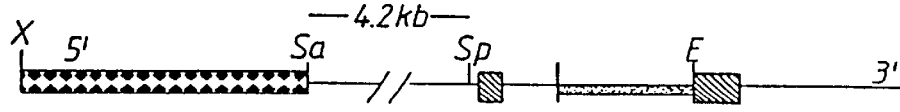

▓▓ pPOLY; ▓▓ pUC18; —— BLG intron or flanking,
▓▓ BLG exons; ▓▓ AAT; | oligo.
E, EcoRI; X, XbaI; Sa, SalI; Sp, SphI; V, EcoRV; St, StyI; P(0), inactivated PvuII site.

Fig. 9g

EXPRESSION OF HUMAN AAT IN TRANSGENIC SHEEP MILK 1 2 3 4 5 6

EXPRESSION OF HUMAN AAT IN THE MILK OF TRANSGENIC MICE 1 2 3 4 5 6 7 8 9 10 11

PRODUCTION OF HETEROLOGOUS PROTEIN IN MILK OF TRANSGENIC NON-HUMAN MAMMALS COMPRISING A CONSTRUCT WITH AN INTRON

This is a divisional of application Ser. No. 08/359,854, filed Dec. 20, 1994, U.S. Pat. No. 5,650,503 which is a continuation of application Ser. No. 07/926,192, filed Aug. 7, 1992, abandoned, which is a continuation of application Ser. No. 07/536,672, filed Sep. 11, 1990, abandoned, which is the U.S. Nat'l phase of international application no. PCT/GB89/01343, filed Nov. 13, 1989.

This invention relates to the production of peptide-containing molecules.

Recombinant DNA technology has been used increasingly over the past decade for the production of commercially important biological materials. To this end, the DNA sequences encoding a variety of medically important human proteins have been cloned. These include insulin, plasminogen activator, alpha$_1$-antitrypsin and coagulation factors VIII and IX. At present, even with the emergent recombinant DNA techniques, these proteins are usually purified from blood and tissue, an expensive and time consuming process which may carry the risk of transmitting infectious agents such as those causing AIDS and hepatitis.

Although the expression of DNA sequences in bacteria to produce the desired medically important protein looks an attractive proposition, in practice the bacteria often prove unsatisfactory as hosts because in the bacterial cell foreign proteins are unstable and are not processed correctly.

Recognising this problem, the expression of cloned genes in mammalian tissue culture has been attempted and has in some instances proved a viable strategy. However batch fermentation of animal cells is an expensive and technically demanding process.

There is therefore a need for a high yield, low cost process for the production of biological substances such as correctly modified eukaryotic polypeptides. The absence of agents that are infectious to humans woutd be an advantage in such a process.

The use of transgenic animals as hosts has been identified as a potential solution to the above problem. WO-A-8800239 discloses transgenic animals which secrete a valuable pharmaceutical protein, in this case Factor IX, into the milk of transgenic sheep. EP-A-0264166 also discloses the general idea of transgenic animals secreting pharmaceutical proteins into their milk, but gives no demonstration that the technique is workable.

Although the pioneering work disclosed in WO-A-8800239 is impressive in its own right, it would be desirable for commercial purposes to improve upon the yields of proteins produced in the milk of the transgenic animal. For Factor IX, for example, expression levels in milk of at least 50 mcg/ml may be commercially highly desirable, and it is possible that for alpha$_1$-antitrypsin higher levels of expression, such as 500 mcg/ml or more may be appropriate for getting a suitably high commercial return.

It would also be desirable if it was possible to improve the reliability of transgenic expression, as well as the quantitative yield of expression. In other words, a reasonable proportion of the initial. Generation 0 (G0) transgenic animals, or lines established from them, should express at reasonable levels. The generality of the technique, in particular, is going to be limited if (say) only one in a hundred animals or lines express. This is particularly the case for large animals, for which, with the techniques currently available, much time and money can be expended to produce only a small number of G0 animals.

Early work with transgenic animals, as represented by WO-A-8800239 has used genetic constructs based on cDNA coding for the protein of interest. The cDNA will be smaller than the natural gene, assuming that the natural gene has introns, and for that reason is more easy to manipulate.

Brinster et al (*PNAS* 85 836–840 (1988)) have demonstrated that introns increase the transcriptional efficiency of transgenes in transgenic mice. Brinster et al show that all the exons and introns of a natural gene are important both for efficient and for reliable expression (that is to say, both the levels of the expression and the proportion of expressing animals) and is due to the presence of the natural introns in that gene. It is known that in some cases this is not attributable to the presence of tissue-specific regulatory sequences in introns, because the phenomenon is observed when the expression of a gene is redirected by a heterologous promoter to a tissue in which it is not normally expressed. Brinster et al say that the effect is peculiar to transgenic animals and is not seen in cell lines.

It might therefore be expected that the way to solve the problems of yield and reliability of expression would be simply to follow the teaching of Brinster et al and to insert into mammalian genomes transgenes based on natural foreign genes as opposed to foreign cDNA. Unfortunately, this approach is itself problematical. First, as mentioned above, natural genes having introns will inevitably be larger than the cDNA coding for the product of the gene. This is simply because the introns are removed from the primary transcription product before export from the nucleus as mRNA. It is technically difficult to handle large genomic DNA. Approximately 20 kb, for example, constitutes the maximum possible cloning size for lambda-phage. The use of other vectors such as cosmids, may increase the handleable size up to 40 kb, but there is then a greater chance of instability. It should be noted that eukaryotic DNA contains repeated DNA sequence elements that can contribute to instability. The larger the piece of DNA the greater the chance that two or more of these elements will. occur, and this may promote instability.

Secondly, even if it is technically possible to manipulate large fragments of genomic DNA, the longer the length of manipulated DNA, the greater chance that restriction sites occur more than once, thereby making manipulation more difficult. This is especially so given the fact that in most transgenic techniques, the DNA to be inserted into the mammalian genome will often be isolated from prokaryotic vector sequences (because the DNA will have been manipulated in a prokaryotic vector, for choice). The prokaryotic vector sequences: usually have to be removed, because they tend to inhibit expression. So the longer the piece of DNA, the more difficult it is to find a restriction enzyme which will not cleave it internally.

To illustrate this problem, alpha$_1$-antitrypsin, Factor IX and Factor VIII will briefly be considered. Alpha$_1$-antitrypsin (AAT) comprises 394 amino acids as a mature peptide. It is initially expressed as a 418 amino acid pre-protein. The mRNA coding for the pre-protein is 1.4 kb long, and this corresponds approximately to the length of the cDNA coding for AAT used in the present application (approximately 1.3 kb). The structural gene (liver version, Perlino et al, The EMBO Journal Volume 6 p.2767–2771 (1987)) coding for AAT contains 4 introns and is 10.2 kb long.

Factor IX (FIX) is initially expressed as a 415 amino acid preprotein. The mRNA is 2.8 kb long, and the cDNA that was used in WO-A-8800239 to build FIX constructs was 1.57 kb long. The structural gene is approximately 34 kb long and comprises 7 introns.

Factor VIII (FVIII) is expressed as a 2,351 amino acid preprotein, which is trimmed to a mature protein of 2,332 amino acids. The mRNA is 9.0 kb in length, whereas the structural gene is 185 kb long.

It would therefore be desirable to improve upon the yields and reliability of transgenic techniques obtained when using constructs based on cDNA, but without running into the size difficulties associated with the natural gene together with all its introns.

It has now been discovered that high yields can be obtained using constructs comprising some but not all, of the naturally occurring introns in a gene.

According to a first aspect of the present invention, there is provided a genetic construct comprising a 5' flanking sequence from a mammalian milk protein gene and DNA coding for a heterologous protein other than the milk protein, wherein the protein-coding DNA comprises at least one, but not all, of the introns naturally occurring in a gene coding for the heterologous protein and wherein the 5'-flanking sequence is sufficient to drive expression of the heterologous protein.

The milk protein gene may be the gene for whey acid protein, alpha-lactalbumin or a casein, but the beta-lactoglobulin gene is particularly preferred.

In this specification the term "intron" includes the whole of any natural intron or part thereof.

The construct will generally be suitable for use in expressing the heterologous protein in a transgenic animal. Expression may take place in a secretory gland such as the salivary gland or the mammary gland. The mammary gland is preferred.

The species of animals selected for expression is not particularly critical, and will be selected by those skilled in the art to be suitable for their needs. Clearly, if secretion in the mammary gland is the primary goal, as is the case with preferred embodiments of the invention, it is essential to use mammals. Suitable laboratory mammals for experimental ease of manipulation include mice and rats. Larger yields may be had from domestic farm animals such as cows, pigs, goats and sheep. Intermediate between laboratory animals and farm animals are such animals as rabbits, which could be suitable producer animals for certain proteins.

The 5' flanking sequence will generally include the milk protein, e.g. beta-lactoglobulin (BLG), transcription start site. For BLG it is preferred that about 800 base pairs (for example 799 base pairs) upstream of the BLG transcription start site be included. In particularly preferred embodiments, at least 4.2 kilobase pairs upstream be included.

The DNA coding for the protein other than BLG ("the heterologous protein") may code for any desired protein of interest. One particularly preferred category of proteins of interest are plasma proteins. Important plasma proteins include serine protease inhibitors, which is to say members of the SERPIN family. An example of such a protein is alpha$_1$-antitrypsin. Other serine protease inhibitors may also be coded for. Other plasma proteins apart from serine protease inhibitors include the blood factors, particularly Factor VIII and Factor IX.

Proteins of interest also include proteins having a degree of homology (for example at least 90%) with the plasma proteins described above. Examples include oxidation-resistant mutants and other analogues of serine protease inhibitors such as AAT. These analogues include' novel protease inhibitors produced by modification of the active site of alpha$_1$-antitrypsin. For example, if the Met-358 of AAT is modified to Val, this replacement of an oxidation-sensitive residue at the active centre with an inert valine renders the molecule resistant to oxidative inactivation. Alternatively, if the Met-358 residue is modified to Arg, the molecule no longer inhibits elastase, but is an efficient heparin-independent thrombin inhibitor (that is to say, it now functions like anti-thrombin III).

The protein-coding DNA has a partial complement of natural introns or parts thereof. It is preferred in some embodiments that all but one be present. For example, the first intron may be missing but it is also possible that other introns may be missing. In other embodiments of the invention, more than one is missing, but there must be at least one intron present in the protein-coding DNA. In certain embodiments it is preferred that only one intron be present.

Suitable 3'-sequences may be present. It may not be essential for such sequences to be present, however, particularly if the protein-coding DNA of interest comprises its own polyadenylation signal sequence. However, it may be necessary or convenient in some embodiments of the invention to provide 3'-sequences and 3'-sequences of BLG will be those of choice. 3'-sequences are not however limited to those derived from the BLG gene.

Appropriate signal and/or secretory sequence(s) may be present if necessary or desirable.

According to a second aspect of the invention, there is provided a method for producing a substance comprising a polypeptide, the method comprising introducing a DNA construct as described above into the genome of an animal in such a way that the protein-coding DNA is expressed in a secretory gland of the animal.

The animal may be a mammal, expression may take place in the mammary gland, for preference. The construct may be inserted into a female mammal, or into a male mammal from which female mammals carrying the construct as a transgene can be bred.

Preferred aspects of the method are as described in WO-A-8800239.

According to a third aspect of the invention, there is provided a vector comprising a genetic construct as described above. The vector may be a plasmid, phage,. cosmid or other vector type, for example derived from yeast.

According to a fourth aspect of the invention, there is provided a cell containing a vector as described above. The cell may be prokaryotic or eukaryotic. If prokaryotic, the cell may be bacterial, for example *E. coli*. If eukaryotic, the cell may be a yeast cell or an insect cell.

According to a fifth aspect of the invention, there is provided a mammalian or other animal cell comprising a construct as described above.

According to a sixth aspect of the invention, there is provided a transgenic mammal or other animal comprising a genetic construct as described above integrated into its genome. It is particularly preferred that the transgenic animal transmits the construct to its progeny, thereby enabling the production of at least one subsequent generation of producer animals.

The invention will now be illustrated by a number of examples. The examples refer to the accompanying drawings, in which:

FIGS. 1 to 9 and 10($a$–$b$) show schematically one strategy used for elaborating fusion genes comprising DNA sequence elements from ovine beta-lactoglobulin and the gene(s) of interest, in this case alpha$_1$-antitrypsin, to be expressed in the mammary gland of a mammal;

EXAMPLE 1

General

Figure 1:
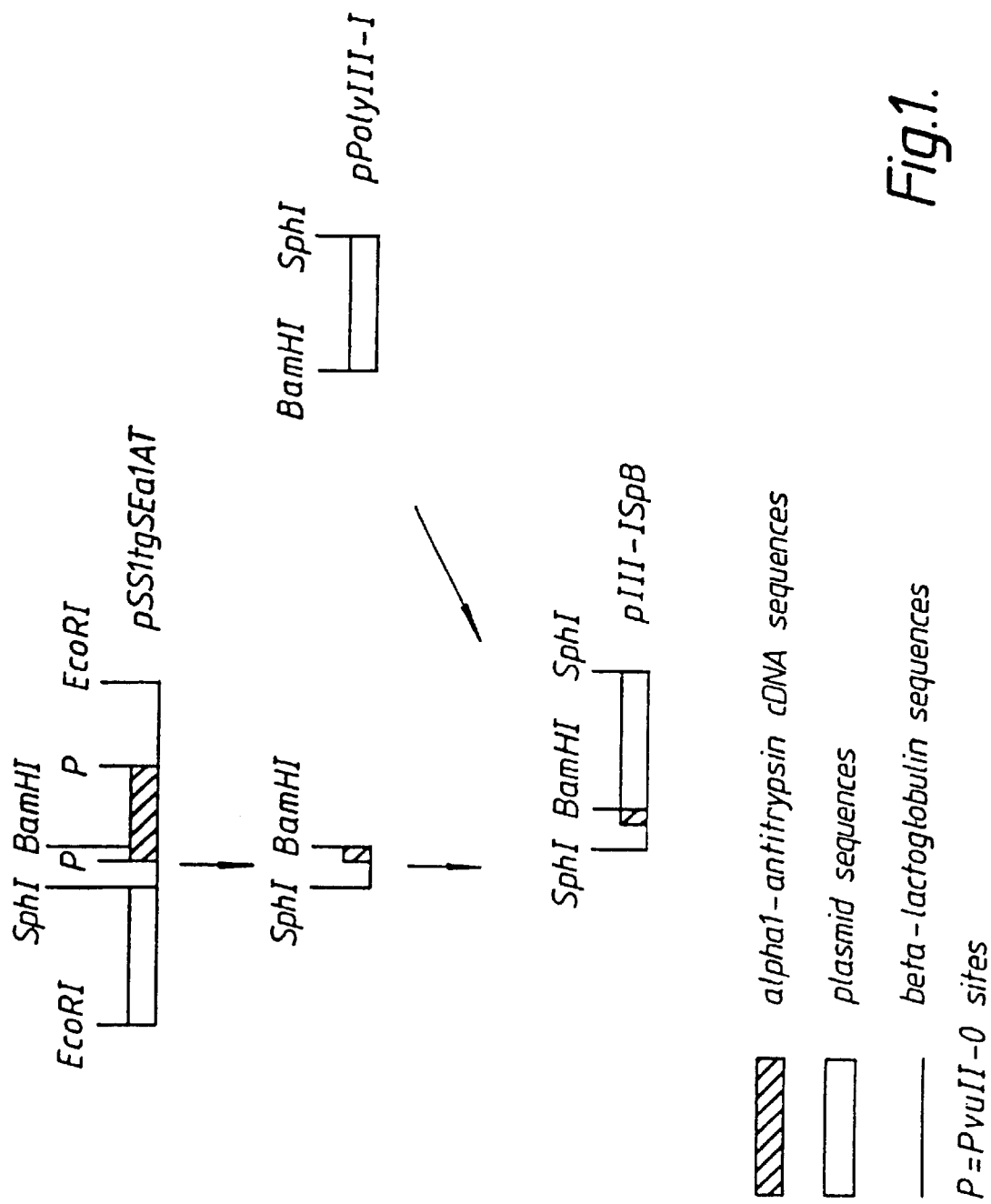
Figure 2:
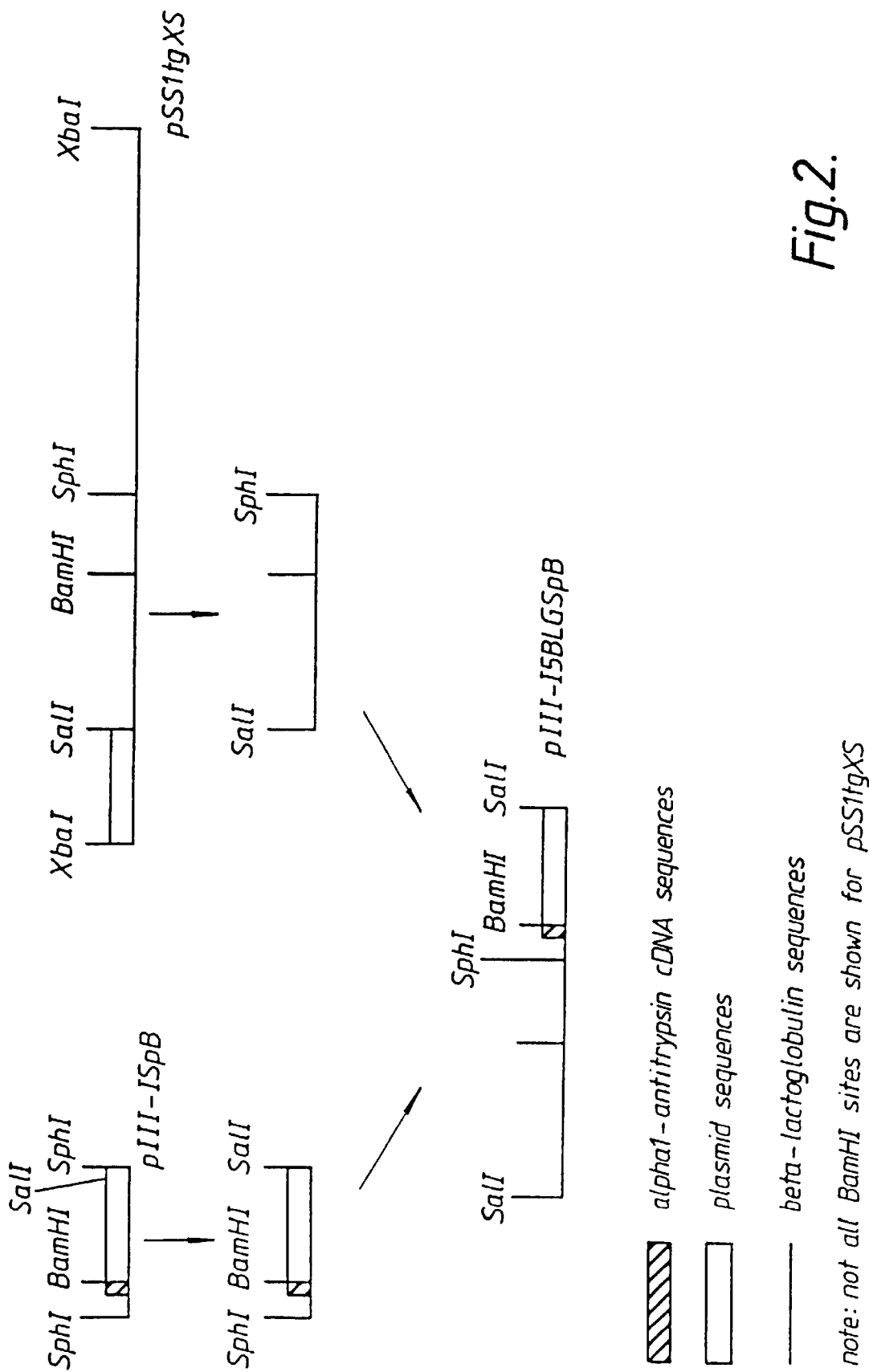
Figure 3:
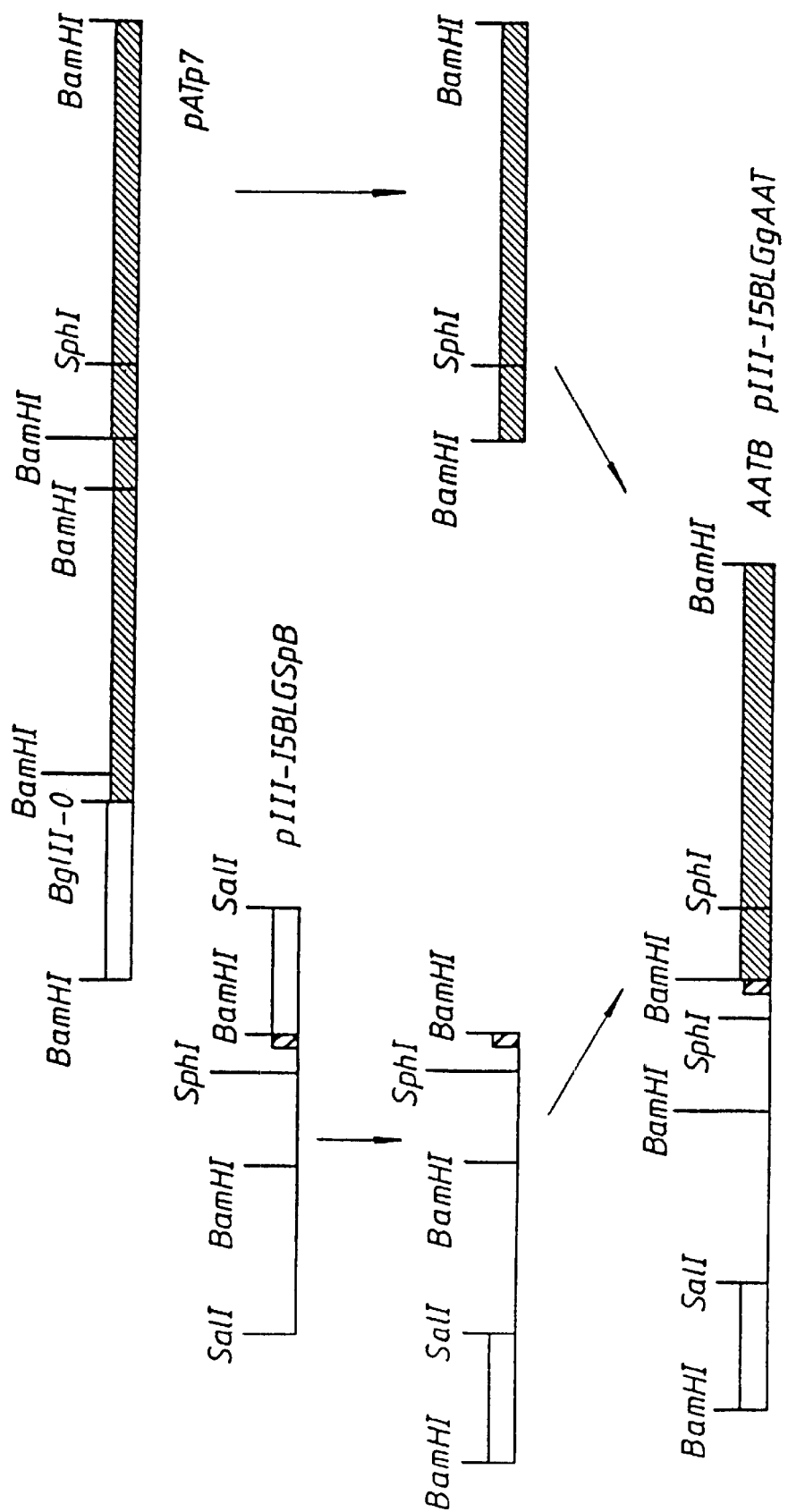
Figure 4:
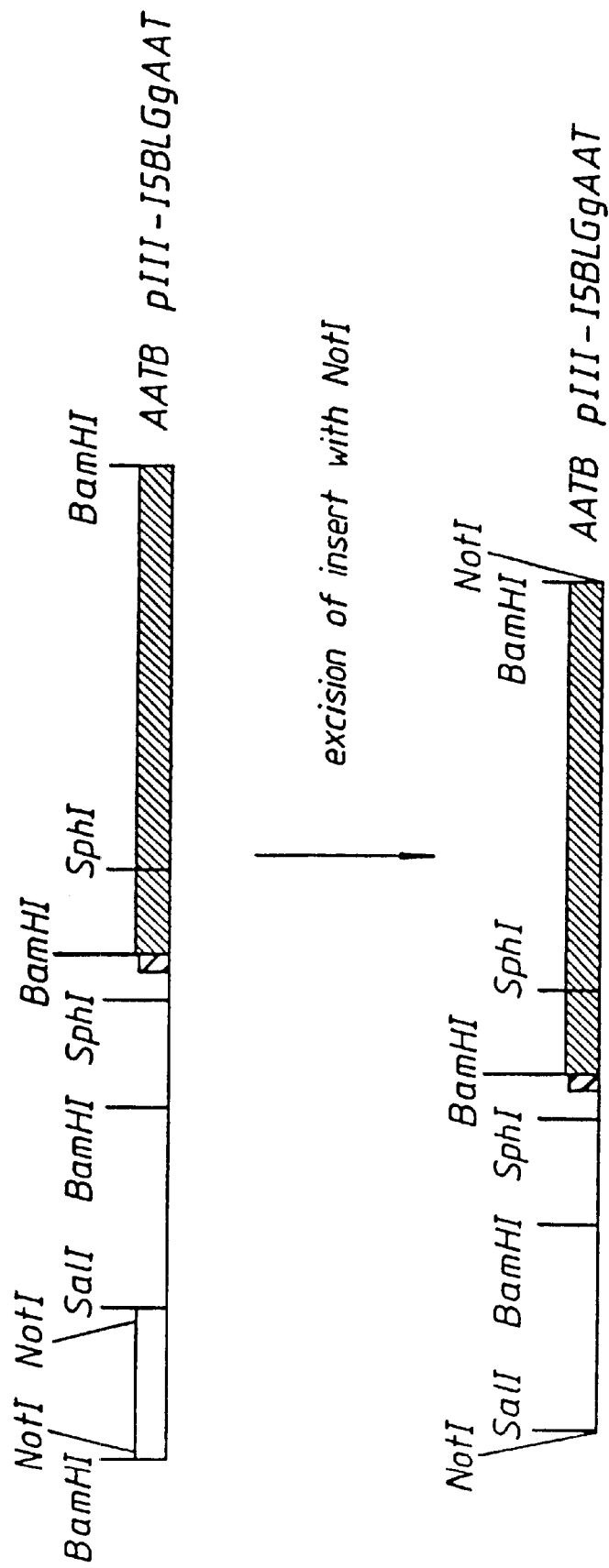
Figure 6:
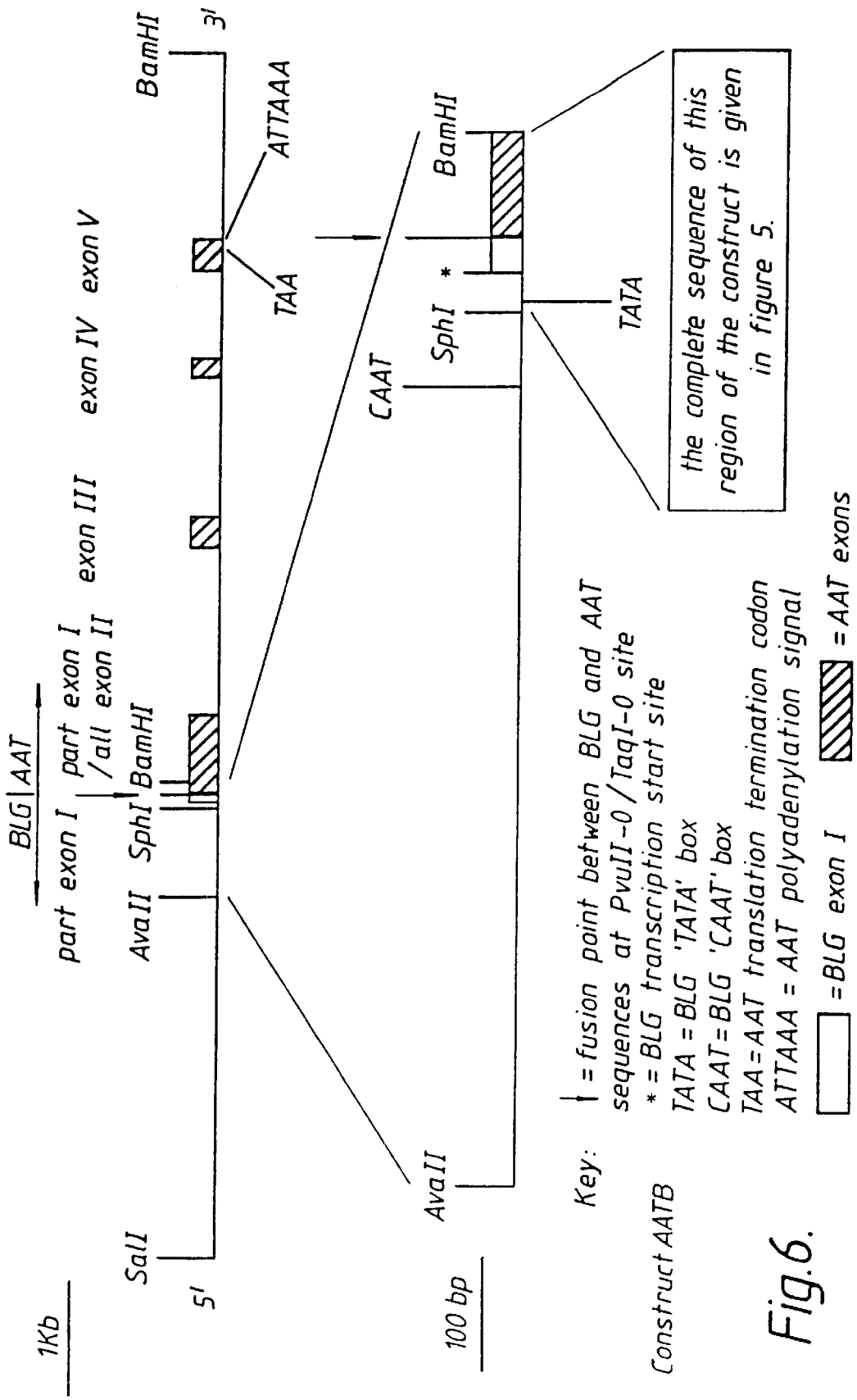

Where not specifically detailed, recombinant DNA and molecular biological procedures were after Maniatis et al ("Molecular Cloning" Cold Spring Harbor (1982)) "Recombinant DNA" *Methods in Enzymology* Volume 68, (edited by R. Wu), Academic Press (1979); "Recombinant DNA part B" *Methods in Enzymology* Volume 100, (Wu, Grossman and Moldgave, Eds), Academic Press (1983); "Recombinant DNA part C" *Methods in Enzymology* Volume 101, (Wu, Grossman and Moldgave, Eds), Academic Press (1983); and "Guide to Molecular Cloning Techniques", *Methods in Enzymology* Volume 152 (edited by S. L. Berger & A. R. Kimmel), Academic Press (1987). Unless specifically stated, all chemicals were purchased from BDH Chemicals Ltd, Poole, Dorset, England or the Sigma Chemical Company, Poole, Dorset, England. Unless specifically stated all DNA modifying enzymes and restriction endonucleases were purchased from BCL, Boehringer Mannheim House, Bell Lane, Lewes, East Sussex BN7 1LG, UK.

[Abbreviations: bp=base pairs; kb=kilobase pairs, AAT= alpha1-antitrypsin; BLG=beta-lactoglobulin; FIX= factor IX; *E. coli=Escherichia coli*; dNTPs= deoxyribonucleotide triphosphates; restriction endonucleases are abbreviated thus e.g. BamHI; the addition of -O after a site for a restriction endonuclease e.g. PvuII-O indicates that the recognition site has been destroyed]

A. PREPARATION OF CONSTRUCTIONS

Elaboration of Beta-Lactoglobulin Fusion Genes

The strategy used for elaborating fusion genes comprising DNA sequence elements from the ovine beta-lactoglobulin and the gene(s) of interest to be expressed in the mammary gland is outlined in FIGS. 1 to 10. The approach utilises sequences derived from a lambda clone, lambdaSS-1, which contains the gene for ovine beta-lactoglobulin, and whose isolation and characterisation is outlined in International Patent Application No. WO-A-8800239 (Pharmaceutical Proteins Ltd) and by Ali & Clark (1988) *Journal of Molecular Biology* 199, 415–426.

The elaboration of seven constructs are -described -AATB, AATA, BLG-BLG, AATC, AATD, FIXD, and DELTA-A2 in sections A1–A7 respectively. Construct AATB constitutes the primary example and the other constructs are included as comparative examples.

The nomenclature eg AATB is generally used to describe the DNA construct without its associated bacterial (plasmid) vector sequences. This form, lacking the vector sequences, corresponds to that microinjected into fertilised eggs and subsequently incorporated into the chromosome(s) of the embryo.

A1 AATB—Construction of pIII-15BLGgAAT

The construct AATB is a hybrid gene which contains sequence elements from the 5'-flanking region of the ovine beta-lactoglobulin gene fused to sequences from the human gene for alpha$_1$-antitrypsin. The features of the AATB construct are summarised in FIG. 6. The sequences from the ovine beta-lactoglobulin gene are contained in a SalI-SphI fragment of about 4.2 kb which contains (by inspection) a putative 'CCAAT box' (AGCCAAGTG) [see Ali & Clark (1988) *Journal of Molecular Biology* 199, 415–426]. In addition there are ovine BLG sequences from this SphI to a PvuII site in the 5'-untranslated region of the BLG transcription unit. The sequence of this SphI-PvuII fragment is shown in FIG. 5. This latter fragment contains a putative 'TATA box' (by inspection) [see Ali & Clark (1988) *Journal of Molecular Biology* 199, 415–426]. The mRNA cap site/ transcription start point CACTCC as determined by S1-mapping and RNase protection assays is also contained within this fragment. Beyond the fusion (PvuII-O) site are found sequences from a cDNA for human alpha$_1$-antitrypsin and from the human alpha$_1$-antitrypsin gene. The sequences from the 5' fusion (TaqI-O) site to the BamHI site 80 bp downstream, include the initiation ATG methionine codon for alpha$_1$-antitrypsin. The first nucleotide (cytosine) in the AAT sequences (CGACAATG . . . , see FIG. 5) corresponds to the last nucleotide in exon I of the AAT gene. The second nucleotide (guanosine) in the AAT sequences (C<u>G</u>ACAATG . . . , see FIG. 5) corresponds to the first nucleotide in exon II of the AAT gene. The exclusion of intron I has been effected by using DNA from a cDNA clone p8α1ppg (see below) as the source of the first 80 bp of the AAT sequences in AATB (TaqI-0 to BamHI). The BamHI site corresponds to that found in exon II of the AAT gene. Beyond this BamHI site are approximately 6.5 kb of the human AAT gene including—the rest of exon II, intron II, exon III, intron III, exon IV, intron IV, exon V and about 1.5 kb of 3'-flanking sequences. Exon V contains the AAT translation termination codon (TAA) and the putative polyadenylation signal (ATTAAA). The signal peptide for the peptide encoded by construct AATB is encoded by the AAT cDNA sequence from <u>ATG</u>CCGTCT to TCCCTG<u>GCT</u> (2 bp upstream from the BanHI site in exon II.

Plasmid pSS1tgSEα1AT

The subclone pSS1tgSEα1AT was constructed as described here and briefly in Example 2 of International Patent Application No. WO-A-8800239 (Pharmaceutical Proteins Ltd). This clone contains the cDNA sequences for human alpha$_1$-antitrypsin inserted into the 5'-untranslated region of the ovine beta-lactoglobulin gene. The plasmid p8α1ppg containing a full length cDNA encoding an M variant of alpha$_1$-antitrypsin was procured from Professor Riccardo Cortese, European Molecular Biology Laboratory, Meyerhofstrasse 1, D-6900 Heidelberg, Federal Republic of Germany (Ciliberto, Dente & Cortese (1985) *Cell* 41, 531–540). The strategy used in the construct BLG-AAT or pSSltgXSTARG, now known as AATA, described in International Patent Application No. WO-A-8800239 (Pharmaceutical Proteins Ltd) required that the polyadenylation signal sequence at the 3' end of the alpha$_1$-antitrypsin cDNA be removed.

The polyadenylation signal was removed in the following manner. Plasmid p8α1ppg DNA was digested with PstI and the digestion products were separated by electrophoresis in a preparative 1% agarose gel containing 0.5 µg/ml ethidium bromide (Sigma). The relevant fragment of about 1400 bp was located by illumination with a UV lamp (Ultra-Violet Products, Inc, San Gabriel, Calif., USA). A piece of dialysis membrane was inserted in front of the band and the DNA fragment subsequently electrophoresed onto the membrane. The DNA was eluted from the dialysis membrane and isolated by use of an 'ElutipD' [Scleicher and Schull, Postfach 4, D-3354, Dassel, W. Germany], employing the procedure recommended by the manufacturer. The gel purified 1400 bp PstI fragment was digested with the TaqI, electrophoresed on a preparative it agarose gel as described above. The TaqI-PstI fragment of approximately 300 bp comprising the 3' end of the alpha$_1$-antitrypsin cDNA including the polyadenylation signal sequence was eluted and purified using an Elutip as described above, as was the TaqI—TaqI fragment of 1093 bp containing the 5' portion of the cDNA. The plasmid vector pUC8 (Pharmacia-LKB Biotechnology, Pharmacia House, Midsummer Boulevard, Central Milton Keynes, Bucks, MK9 3HP, UK) was digested with AccI and PstI, phenol/chloroform extracted and DNA recovered by ethanol precipitation. The 300 bp TaqI-PstI fragment from p8α1ppg was ligated using T4 DNA ligase to pUC8 cut with AccI and PstI and the ligation products were used to transform E. coli strain DH-1 (Gibco-BRL, P0 Box 35, Trident House, Renfrew Road, Paisley PA3 4EF, Scotland, UK) to ampicillin resistance. Plasmid DNA was isolated from ampicillin resistant colonies. The correct recombinants were identified by the release of a fragment of approximately 300 bp on double digestion with AccI and PstI. The plasmid generated was called pUC8.3'AT.3.

Plasmid pUC8.3'AT.3 was subjected to partial digestion with BstNI and the fragment(s) corresponding to linearised pUC8.3'AT.3 isolated from an agarose gel. There are seven BstNI sites in pUC.3'AT.3, five in the vector and two in the region corresponding to the 3'-untranslated sequences of alpha$_1$-antitrypsin. The BstNI linearised and gel purified DNA was digested with PstI which cuts in the pUC8 polylinker where it joins the 3' end of the cDNA insert. The PstI digested DNA was end repaired with T4 DNA polymerase in the presence of excess dNTPs and self-ligated with T4 DNA ligase. The BstNI-PstI fragment containing the: polyadenylation signal sequence is lost by this procedure. The ligated material was used to transform. E. coli strain DH-1 to ampicillin resistance. Plasmid DNA was isolated from ampicillin resistant colonies. The correct clone was identified by restriction analysis and comparison with pUC8.3'AT.3. The correct clone was characterised by retention of single sites for BamHI and HindIII, loss of a PstI site, and a reduction in the size of the small PvuII fragment. The correct clone was termed pB5.

Plasmid pB5 DNA was digested with AccI, phenol/chloroform extracted and DNA recovered by ethanol precipitation. AccI cleaved pB5 DNA was treated with calf intestine alkaline phosphatase (BCL). The reaction was stopped by adding. EDTA to 10 millimolar and heating at 65° C. for 10 minutes. The DNA was recovered after two phenol/chloroform and one chloroform extractions by precipitation with ethanol. T4 DNA ligase was used to ligate the 1093 bp TaqI—TaqI fragment described above to pB5, AccI cleaved and phosphatased DNA and the ligation products were used to transform E. coli strain HB101 (Gibco-BRL) to ampicillin resistance. The identity of the correct clone (pUC8α1AT.73) was verified by restriction analysis—presence of a 909 bp HinfI fragment, a 1093 bp TaqI fragment, and a 87 bp BamHI fragment.

The alpha$_1$-antitrypsin cDNA minus its polyadenylation signal was excised from pUC8α1AT.73 as a 1300 bp AccI-HindIII fragment and isolated from a preparative gel. The 1300 bp AccI-HindIII fragment was end-repaired with the klenow fragment of E. coli DNA polymerase in the presence of excess dNTPs. The fragment was ligated into PvuII restricted, phosphatase treated pSS1tgSE DNA (see International Patent Application No. WO-A-8800239 (Pharmaceutical Proteins Ltd) to form pSS1tgSEα1AT after transforming E. coli DH-1 to ampicillin resistance.

Plasmid pIII-ISpB (see FIG. 1) pSS1tgSEα1AT DNA was linearised by digestion with sphI which cuts at a unique site in the plasmid in a region of DNA corresponding to the 5' flanking sequences of the beta-lactoglobulin transcription unit. The DNA was recovered after phenol/chloroform extractions by precipitation with ethanol. The SphI linearised plasmid was digested with BamHI which cuts at a unique site in the plasmid in a region of DNA corresponding to the mRNA sequences of alpha$_1$-antitrypsin. The 155 bp SphI-BamHI fragment, comprising beta-lactoglobulin sequences fused to alpha$_1$-antitrypsin sequences was located in a 1% agarose gel and isolated by use of an ElutipD as described above.

The plasmid pIII-ISpB was constructed by using T4 DNA ligase to ligate the 155 bp SphI-BamHI fragment from subclone pSS1tgSEα1AT into the plasmid vector pPolyIII-I (Lathe, Vilotte & Clark, 1987, Gene 57, 193–201) which had been digested with SpHI and BamHI. [The vector pPolyIII-I is freely available from Dr. A. J. Clark, AFRC Institute of Animal Physiology and Genetics Research, West Mains Road, Edinburgh EH9 3JQ, UK.] Clones were isolated after transforming competent E. coli DH5a cells (Gibco-BRL) to ampicillin resistance. Plasmid DNA was prepared from the ampicillin resistant colonies and screened for the desired product pIII-ISpB was confirmed as the desired product by the retention of cleavage sites for the enzymes BamHI and SphI and by the addition (when compared to the vector pPolyIII-I) of a cleavage site for the enzyme StuI. The StuI site is present in the 155 bp SphI-BamHI fragment isolated from pSS-1tgSEα1AT.

Plasmid pIII-15BLGSpB (pAT2-3) (see FIG. 2) pIII-ISpB DNA was digested with the SphI and SalI.

SphI cuts at a unique site in the plasmid in a region of DNA corresponding to the 5' flanking sequences of the beta-lactoglobulin transcription unit. This site represents the junction between the beta-lactoglobulin sequences and the plasmid vector sequences. SalI cuts at a unique site in the plasmid in the vector polylinker sequences. The SphI/SalI digested pIII-ISpB DNA was electrophoresed on a preparative 1% agarose gel as described above. The SalI-SphI fragment of approximately 2.2 kb was eluted and purified using an Elutip as described above.

The plasmid DNA pSS-1tgXS (described in International Patent Application No. WO-A-8800239 (Pharmaceutical Proteins Ltd)) was digested with SpHI and SalI and the DNA electrophoresed on a 0.9% agarose gel. The relevant SalI-SphI fragment, comprising approximately 4.2 kb of DNA sequences from the 5' flanking sequences of the beta-lactoglobulin gene, was located by illumination with ultra violet light and recovered by use of an Elutip as described above.

The plasmid pIII-15BLGSpB was constructed by using T4 DNA ligase to ligate the 4.2 kb SalI-SphI fragment described above into gel purified SalI-SphI digested pIII-ISpB DNA. Clones were isolated after transforming E. coli DH5 (Gibco-BRL) to ampicillin resistance. Plasmid DNA was prepared from the ampicillin resistant colonies and screened for the desired product. The correct product was verified by the presence of two BamHI sites—one in the 4.2 kb fragment containing the 5' flanking sequences of beta-lactoglobulin and one in the sequences corresponding to the alpha$_1$-antitrypsin mRNA. Cleavage of the correct product with BamHI yields two fragments including one of approximately. 1.75 kb which spans the cloning junctions (see FIG. 2).

Plasmid pIII-15BLGgAAT (AATB or G7) (see FIG. 3) An alpha$_1$-antitrypsin DNA clone pATp7 was procured from Dr. Gavin Kelsey, MRC Human Biochemical Genetics Unit, The Galton Laboratory, University College London, Wolfson House, 4 Stephenson Way, London NW1 2HE, UK. This clone contains the entire alpha$_1$-antitrypsin transcription unit plus 348 bp of 5' and approximately 1500 bp of 3' flanking sequences as an insert of approximately 12.3 kb in the BamHI site of a plasmid vector pUC9 (Pharmacia-LKB Biotechnology, Pharmacia. House, Midsummer Boulevard, Central Milton Keynes, Bucks, MK9 3HP, UK). The insert for clone pATp7 was prepared by partial BamHI and partial BglII digestion of cbsmid clone aATcl (Kelsey, Povey, Bygrave & Lovell-Badge (1987) *Genes and Development* 1, 161–171). The clone pATp7 contains the gene which encodes the M$_1$ allele, which is the most frequent at the Pi locus. Most of the DNA sequence of this gene is reported by Long, Chandra, Woo, Davie & Kurachi (1984) *Biochemistry* 23, 4828–4837.

Plasmid DNA from pATp7 was digested with BamHI and electrophoresed in a 0.9% agarose gel. The relevant BamHI fragment, comprising approximately 6500 bp of alpha$_1$-antitrypsin sequences from the BamHI site in exon II of this gene to a BamHI site in the 3' flanking region was located and purified by use of an Elutip as described above.

The plasmid pIII-15BLGSpB (also known as AT2-3) was linearised by partial digestion with BamHI. There are two BamHI sites in this plasmid one in the sequences corresponding to the 5' flanking sequences of beta-lactoglobulin and the other in the sequences corresponding to the mRNA for alpha$_1$-antitrypsin. The latter site is the desired site for insertion of the 6500 bp BamHI fragment from pATp7. The products of the partial BamHI digestion of plasmid pIII-15BLGSpB were electrophoresed in a 0.9% agarose gel. The fragment(s) corresponding to linearised pIII-15BLGSpB were located and purified using an Elutip as described above. It is expected that this fragment preparation will contain the two possible BamHI linearised molecules. BamHI linearised, gel purified DNA was dissolved in TE (10 mM Tris.HCl, 1 mM EDTA pH 8) and treated with calf intestinal phosphatase (BCL) for 30 minutes at 37° C. The reaction was stopped by adding EDTA to 10 millimolar and heating at 65° C. for 10 minutes. The DNA was recovered after two phenol/chloroform and one chloroform extractions by precipitation with ethanol.

The plasmid pIII-15BLGgAAT was constructed by using T4 DNA ligase to ligate the 6500 bp BamHI fragment from pATp7 into BamHI linearised, gel purified and phosphatase treated pIII-15BLGSpB DNA. Clones were isolated after transforming *E. coli* DH-5 (Gibco-BRL) to ampicillin resistance. Plasmid DNA was purified from the ampicillin resistant colonies and screened for the desired product. The desired clones were characterised by restriction analysis and, in particular, by the presence of an SphI fragment of approximately 1.6 kb. Plasmid DNA was prepared for one such clone (G7) and given the nomenclature pIII-15BLGgAAT (also known as AATB).

The diagnostic 1.6kb SphI fragment was subcloned from pIII-15BLGgAAT into the SphI site of the M13 vector M13tg130 (Kieny, Lathe & Lecocq (1983) *Gene* 26, 91–99). The DNA sequence of 180 nucleotides from the SphI site corresponding to that in the 5' flanking region of the beta-lactoglobulin gene in a 3' direction through the fusion point of the beta-lactoglobulin and. alpha$_1$-antitrypsin sequences was determined by the chain terminator reaction using a Sequenasetm kit (USB, United States Biochemical Corporation, PO Box 22400, Cleveland, Ohio 44122, USA) according to the manufacturers instructions. The sequence of this region is given in FIG. 5.

Preparation of DNA for microinjection (see FIG. 4) The β-lactoglobulin/αl-antitrypsin fusion gene insert was excised from pIII-15BLGgAAT as follows. 25–50 μg aliquots of pIII-15BLGgAAT plasmid DNA were digested with NotI and the digested material electrophoresed on a 0.6% agarose gel. The larger fragment of approximately 10.5 kb was visualised under ultra-violet light and purified-using an Elutip as described above. Following ethanol precipitation of the DNA eluted from the Elutip, the DNA was further purified as follows. The DNA was extracted once with phenol/chloroform, once with chloroform and was then precipitated with ethanol twice. The DNA was washed with 70% ethanol, dried under vacuum and dissolved in TE (10 mM Tris.HCI, lmM EDTA pH 8). All aqueous solutions used in these later stages had been filtered through a 0.22 μm filter.

Pipette tips were rinsed in filtered sterilised water prior to use. The DNA concentration of the purified insert was estimated by comparing aliquots with known amounts of bacteriophage lambda DNA on ethidium bromide stained agarose gels. The insert DNA was checked for purity by restriction mapping.

A2 AATA—Construction of pSS1tgXSα1AT

The construct AATA is analogous to the construct BLG-FIX or pSS1tgXSFIX described in International Patent Application No. WO-A-8800239 (Pharmaceutical Proteins Ltd). The elaboration of AATA is outlined in Example 2 of International Patent Application No. WO-A-8800239 (Pharmaceutical Proteins Ltd) as a second example of the generalised construct pSS1tgXSTARG. The first stages of the construction of AATA (ie the generation of the plasmid pSS1tgSEα1AT) are described above in section A1.

Figure 7A:
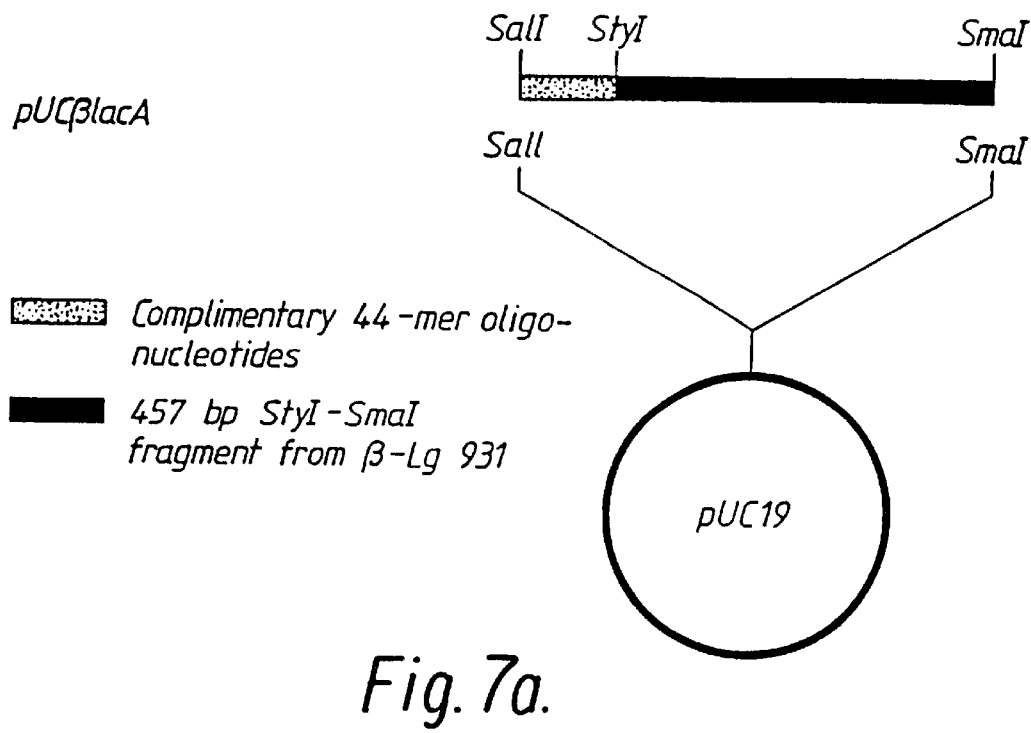
Figure 7B:
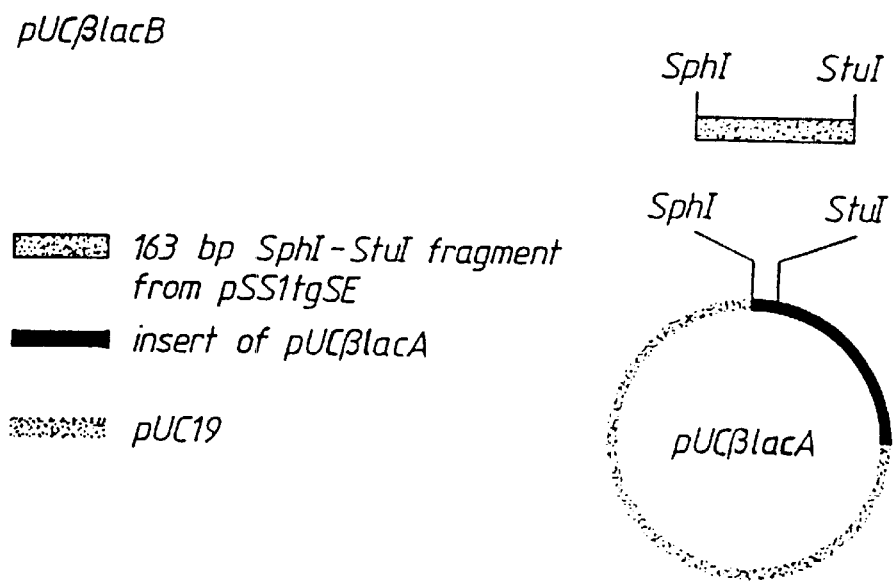
Figure 8A:
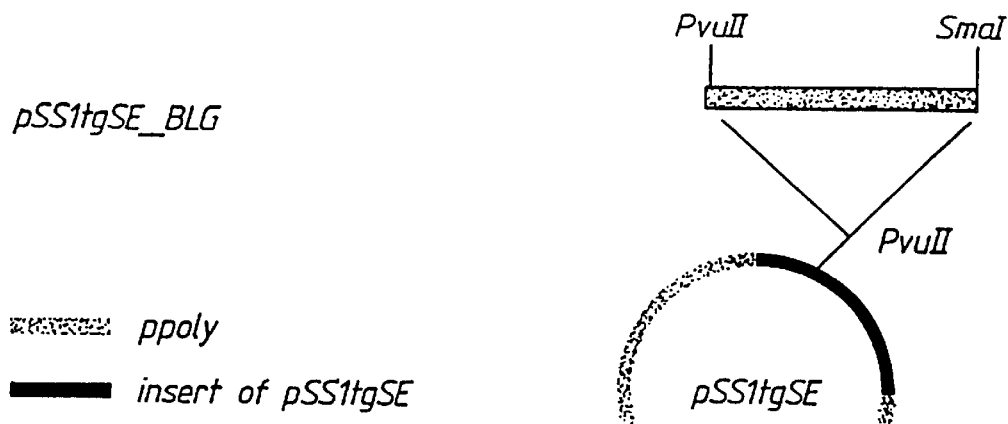
Figure 8B:
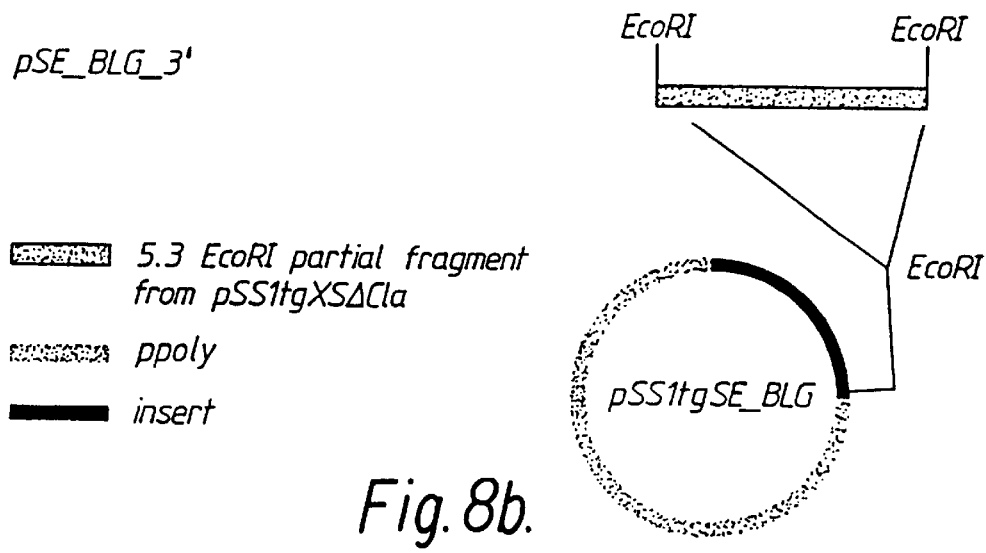
Figure 8C:
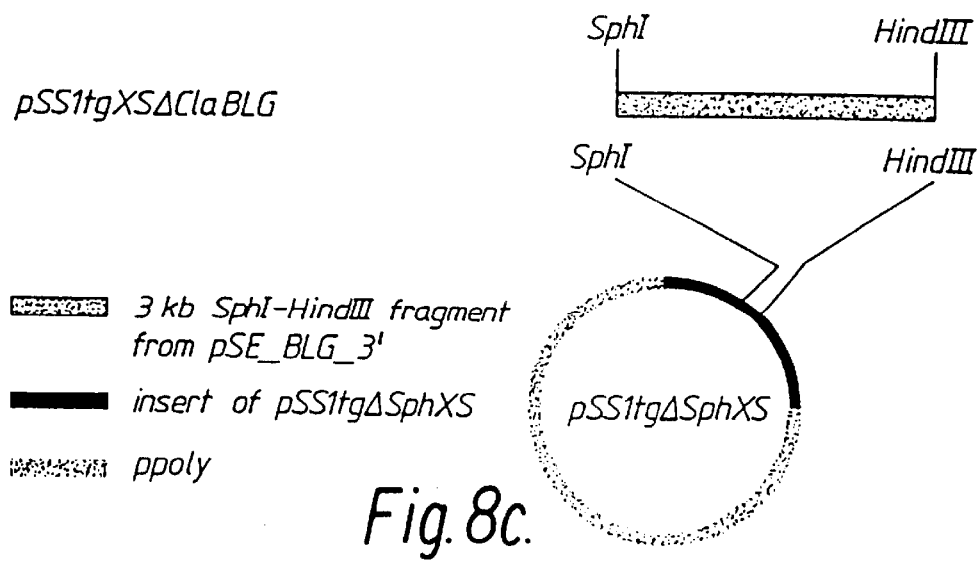

A3 BLG-BLG—Construction of pSS1taXSDELTAClaBLG (see FIGS. 7 and 8)

The construct is analogous to FIXA and AATA (generally designated as pSS1tgXSTARG and specifically as BLG-FIX and BLG-AAT in patent WO-A-8800239) ie, the cDNA for ovine β-lactoglobulin has been inserted into the PvuII site in the first exon of pSS1tgXSDELTACla (see below). pSS1tgXSDELTACla is a variant of pSS1tgXS lacking the ClaI restriction site found in exon 3 which should cause a frameshift in the 2nd open reading frame in the expected bicistronic message of BLG-BLG and premature termination of any polypeptide being translated. It was necessary to sabotage the 2nd open reading frame in this manner in order that the polypeptides encoded by the two open reading frames could be distinguished. In order to generate this construct a full length BLG cDNA had first to be made.

pUCβlacA

Two complimentary 44-mer oligonucleotides, synthesised by the Oswell DNA Service, Department of Chemistry, University of Edinburgh, and containing bases 117–159 of the ovine β-lactoglobulin cDNA sequence (Gaye et al, (1986) *Biochimie* 68, 1097–1107) were annealed to generate SalI and StyI complimentary termini. The annealed oligonucleotides were then ligated using T4 DNA ligase to equimolar amounts of a gel purified 457 bp StyI-SmaI fragment from β-Lg 931 (Gaye et al, op cit) and gel purified pUC19 (Pharmacia-LKB Biotechnology, Pharmacia House, Midsummer Boulevard, Central Milton Keynes, Bucks, MK9 3HP, UK) which had been digested with SalI-SmaI. After transformation of competent *E. coli* strain JM83 (see Messing (1979) Recombinant DNA Technical Bulletin, NIH Publication No. 79–99, 2, No. 2 (1979), 43–48) the correct recombinant was determined by restriction analysis.

pUCβlacB pUCβlacA digested with SphI and StuI was ligated to equimolar amounts of a gel purified 163 bp SphI-Stul fragment from pSS1tgSE (described in patent WO-A-8800239) using T4 DNA ligase. After transformation of competent *E. coli* strain JM83 the correct recombinant was determined by restriction analysis.

pSS1tgXSDELTACla

After transformation of competent *E. coli* strain DL43 (relevant phenotype dam⁻, dcm⁻; also called GM119, gift of Dr. D. Leach, Department of Molecular Biology, University of Edinburgh, West Mains Road, Edinburgh EH9, UK) with the plasmid pSSltgXS plasmid DNA was isolated and digested to completion with ClaI. The DNA termini were end-repaired using the Klenow fragment of *E. coli* DNA polymerase in the presence of excess dNTP's prior to ligation with T4 DNA ligase in the presence of 1 mM hexamine cobalt chloride, 25 mM KCI ([to encourage self-ligation (Rusche & Howard-Flanders (1985) *Nucleic Acids Research* 13, 1997–2008)]). The ligation products were used to transform competent DL43 and ClaI deficient recombinants were confirmed by restriction analysis.

pSS1tgSE_BLG

Equimolar amounts of gel purified pSS1tgSE, digested to completion with PvuII and dephosphorylated with Calf intestinal phosphatase (BCL), were ligated to a gel purified 580 bp PvuII-SmaI fragment from pUCAlacB using T4 DNA ligase. After transformation of competent DH5α (Gibco-BRL) the correct recombinant was confirmed by restriction analysis.

pSE_BLG_3'

Equimolar amounts of gel purified pSS1tgSE_BLG digested to completion with EcoRI were ligated to 3 (~4.3–5.3) gel purified products of a partial EcoRI digestion of pSS1tgXSDELTACla using T4 DNA ligase. After transformation of competent DH5α (Gibco-BRL) the correct recombinant was identified by restriction analysis.

pSS1tgXSDELTAClaBLG

The gel purified ~3 kb SphI-HindIII fragment from pSE_BLG_3' was ligated to equimolar amounts of gel purified ~9.6 kb SphI-HindIII fragment from pSS1tgDELTASphXS (a derivative of pSSltgXS lacking the SphI restriction site in the polylinker region of the vector pPolyl) using T4 DNA ligase. After transformation of competent DL43 the construct was confirmed by restriction analysis.

Isolation of DNA fragment for microinjection pSS1tgXSDELTAClaBLG was digested to completion with BglII and XbaI to pSS1tgXSDELTAClaBLG was digested to completion with BglII and XbaI to liberate the insert from the vector. The insert was recovered from an agarose gel by electroelution onto dialysis membrane (Smith (1980) *Methods in Enzymology* 65, 371–380). After release from the membrane the DNA was phenol/chloroform extracted, ethanol precipitated and -resuspended in 100 µl H$_2$O ready for microinjection.

A4 AATC—Construction of pSS1pUCXSTGA.AAT (see FIG. 9)

This construct contains the cDNA sequences encoding human alpha-1-antitrypsin (AAT) inserted into the second exon of the ovine β-lactoglobulin (BLG) gene. The aim was to determine whether or not inserting the AAT cDNA sequences at a site distant from the BLG promoter would improve the levels of expression. As such, this construct comprises the intact first exon and first intron of the BLG gene.

Since this construct contains two ATG codons (including the normal BLG initiating methionine) in the first BLG exon (ie before the sequences encoding AAT) an 'in-frame' termination codon (TGA) was introduced at the junction point between BLG and AAT. This was thought necessary to prevent the production of a fusion protein between BLG and AAT. It will be noted that for AAT protein to be produced from the expected transcripts, reinitiation(at the natural initiating ATG of AAT) of transcription will have to take place after termination at this codon.

pSS1tgSE.TGA

Two oligonucleotides (5'CTTGTGATATCG3' and 5'AATTCGATATCAC3') were synthesised by the Oswell DNA Service, Department of Chemistry, University of Edinburgh. After annealing, the oligonucleotides comprise a TGA stop codon, an EcoRV site and have cohesive ends for a StvI and an EcoRI site, respectively. The annealed oligonucleotides were ligated to a gel purified StyI-EcoRI fragment of about 3.2 kb isolated from pSS1tgSE (pSS1tgSE is described in International Patent Application No. WO-A-8800239 (Pharmaceutical Proteins ltd)). This will insert these sequences at the StyI site which comprises nucleotides 20–25 of BLG-exon II and generates the plasmid pSS1tgSE.TGA, in which the TGA stop codon is 'in frame' with the sequences encoding BLG. Note the sequences 3' to the BLG StyI site are replaced by the oligonucleotides in this step. The ligation products were used to transform *E.coli* strain DH5α (Gibco-BRL) to ampicillin resistance. The correct clone (pSS1tgSE.TGA) was identified by restriction analysis—retention of sites for EcoRI and SphI and acquisition of a site for EcoRV.

pSS1tgSpX.TGA pSS1tgSE.TGA was cleaved with EcoRI and the cohesive termini were end-repaired by filling in with Klenow fragment of *E. coli* DNA polymerase in the presence of excess dNTPs. After end-repair the preparation was cleaved with SphI and the insert fragment of about 800 bp (now SphI→EcoRI (blunt)) was isolated on a preparative gel. Plasmid pBJ7 (this patent, see below, section A4) was cleaved with SpHI and PvuII and the larger (about 4.3 kb) fragment isolated. Note that this fragment contains the pPolyl vector sequences. The SphI-EcoRI (blunt) fragment excised from pSS1tgSE.TGA was ligated using T4 DNA ligase to the SphI-PvuII fragment isolated from pBJ7 and the ligation products used to transform *E. coli* strain DH5α (Gibco-BRL) to ampicillin resistance. The correct recombinant plasmid pSS1tgSpX.TGA, which contains exon I, intron I, part exon II, oligonucleotide, part exon 5 and exons 6 and 7 of the BLG gene, was identified by restriction analysis.

pSS1pUCXS.TGA

The BLG 5' SaII-SphI fragment of about 4.2 kb was isolated from pSSItgXS (WO-A-8800239) and ligated to equimolar amounts of the SphI-XbaI insert from pSS1tgSpX.TGA and SaII-XbaI cleaved plasmid vector pUC18 (Pharmacia-LKB Biotechnology, Pharmacia House, Midsummer Boulevard, Central Milton Keynes, Bucks, MK9 3HP, UK). The ligation products were used to transform *E. coli* strain DH5α (Gibco-BRL) to ampicillin resistance. The correct clone, pSS1pUCXS.TGA, was identified by restriction analysis.

pSS1pUCXSAAT.TGA (AATC)

pSS1pUCXS.TGA contains a unique EcoRV site (derived from the oligonucleotide) inserted in the second exon which will cleave this plasmid 1 bp downstream of the 'in-frame' TGA. cDNA sequences can thus be inserted into this plasmid downstream of the BLG sequences in the second exon. This is exemplified by the construction of pSS1pUCXSAAT.TGA (AATC) in which AccI-HindIII fragment derived from pUC8αLAT.73 (this patent, see Section A1 above) was inserted at the EcoRV site. Plasmid pUC8α1AT.73 (described in section A1above) was digested with AccI and HindIII and the resulting fragment containing the alpha$_1$-antitrypsin cDNA minus its polyadenylation signal was end-repaired using Klenow fragment of *E. coli* DNA polymerase in the presence of excess dNTPs. This blunt ended fragment was gel purified and ligated using T4 DNA ligase to gel purified pSS1pUCXS.TGA cleaved with ECORV and dephosphorylated to prevent recircularisation. After transformation of competent *E. coli* strain DH5α (Gibco-BRL) with the ligation products, the correct clone was identified by restriction enzyme analysis.

Figure 10A:
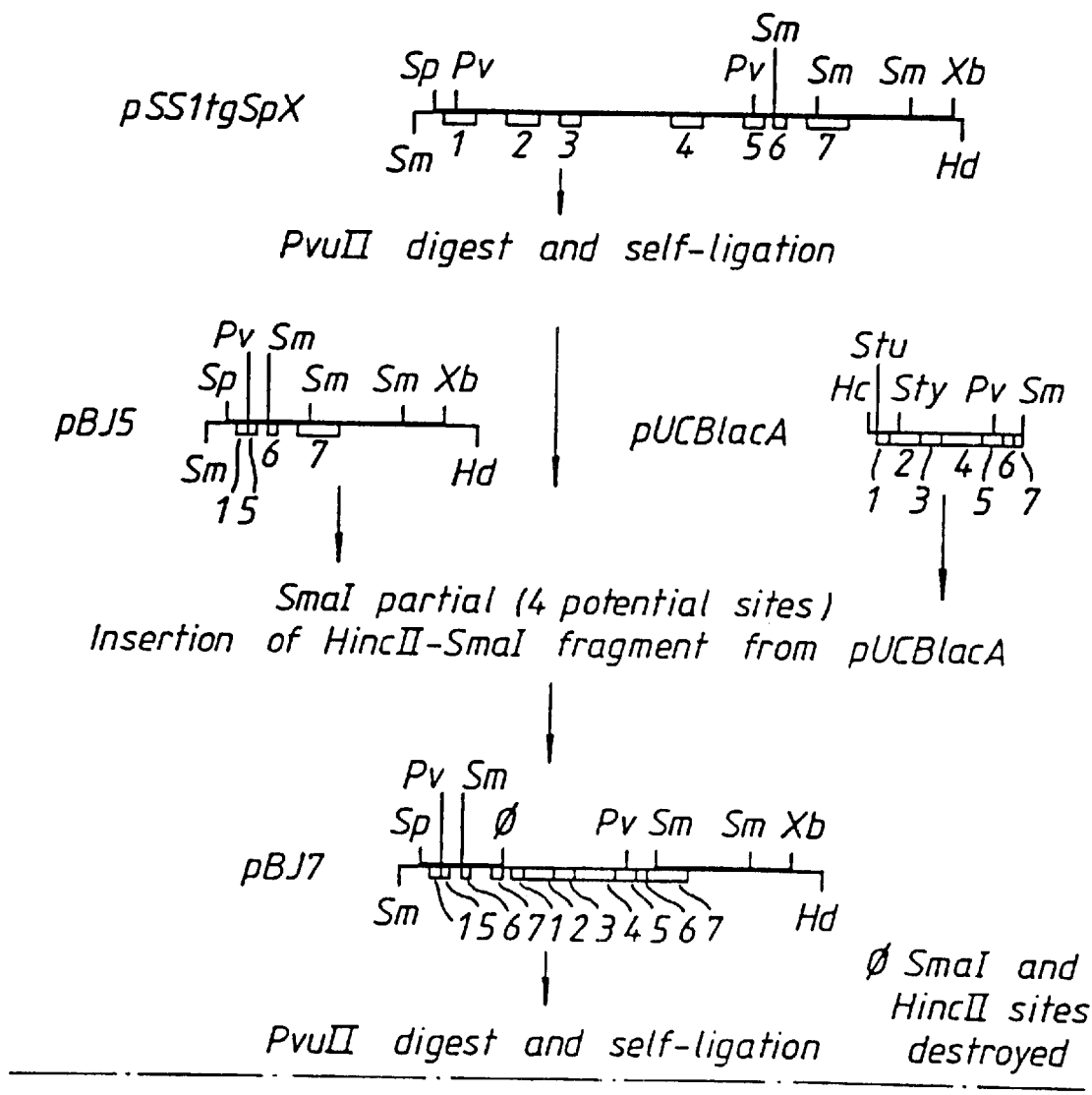
Figure 10B:
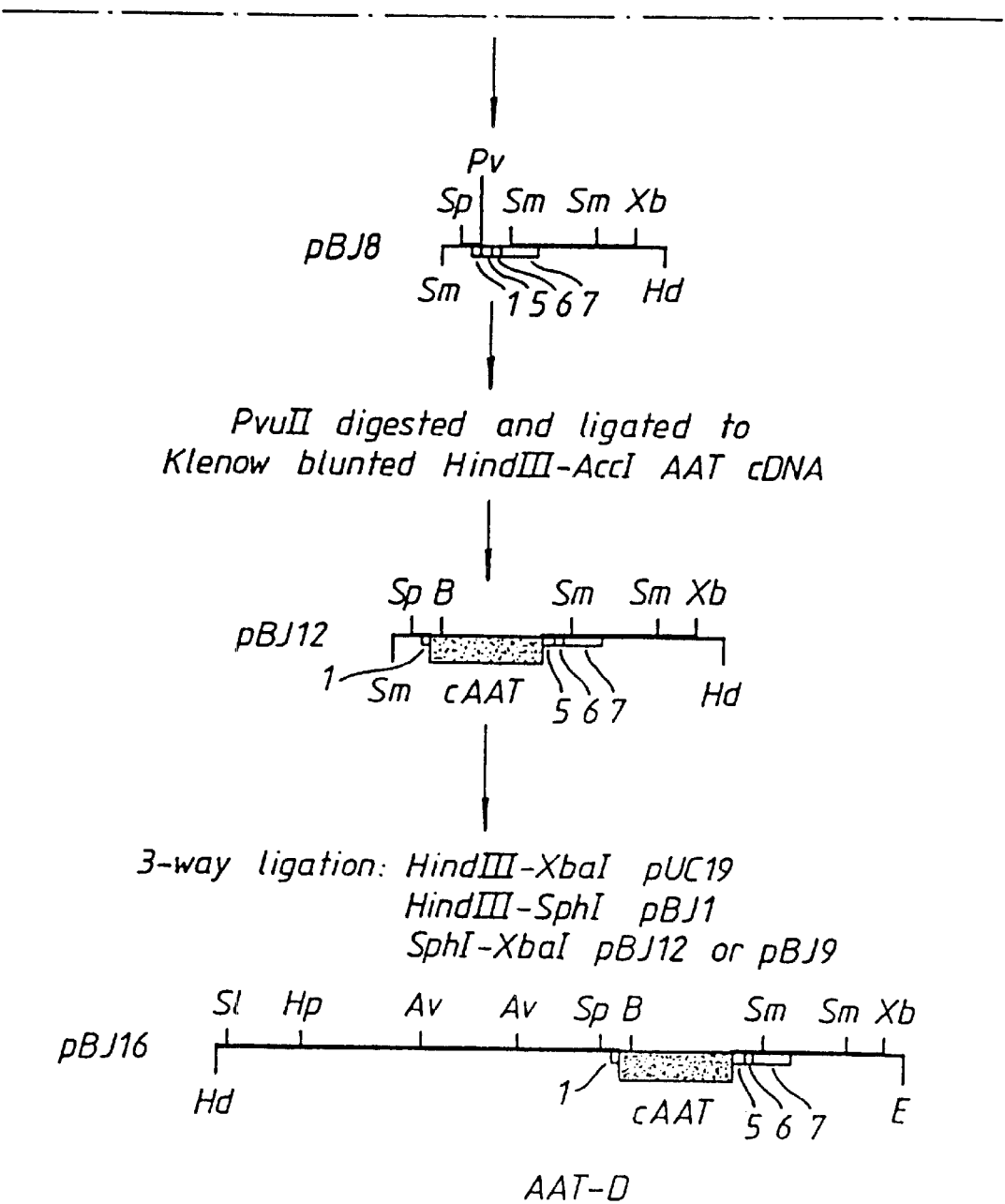

A5 Construction of AATD (pBJ16) (see FIG. 10)

This construct contains the cDNA for human alpha$_1$-antitrypsin flanked by BLG sequences. The 5' flanking sequences include the SalI to PvuII-0 BLG sequences also present in AATA and AATB. The fusion point between the BLG and AAT sequences is in the 5'-untranslated region of the BLG first exon as is the case in AATA, FIXA and AATB. The 3' flanking sequences comprise exons 6 and 7 of BLG and the 3' flanking sequences of the BLG gene as far as the XbaI site. This construct contains no introns and was designed to examine whether the 5' and 3' BLG sequences described above are sufficient to direct efficient mammary specific expression of cDNAs encoding human plasma proteins as exemplified by that for AAT.

Plasmid pSS1tgSpX

The gel purified SphI-XbaI restriction fragment of about 6.6 kb from pSS1tgXS (described in patent WO-A-8800239) was ligated using T4 DNA ligase to gel purified pPolyI (Lathe, Vilotte & Clark, 1987, *Gene* 57, 193–201) (also described in patent WO-A-8800239) digested with SphI and XbaI. [The vector pPolyI is freely available from Professor R. Lathe, LGME-CNRS and U184 INSERM, 11 rue Humann, 67085, Strasbourg, France.] After transformation of competent *E. coli* strain DHRα (Gibco-BRL) the correct clone was identified by restriction enzyme analysis.

Plasmid pBJ5

The gel purified PvuII restriction fragment containing the origin of replication from pSS1tgspX was self-ligated using T4 DNA ligase in the presence of 1 mM hexamine cobalt chloride, 25 mM KCI [to encourage self-ligation (Rusche & Howard-Flanders (1985) *Nucleic Acids Research* 13, 1997–2008)]. After transformation of competent *E. coli* strain DHRα (Gibco-BRL) the correct clone was identified by restriction enzyme analysis.

Plasmid pUCβlacA

See Example 1 A3 for a Description of pUCβlacA

Plasmid pBJ7

The gel purified HincII-SmaI restriction fragment from pUCβlacA was ligated using T4 DNA ligase to gel purified pBJ5 linearised by partial digestion with SmaI. After transformation of competent *E. coli* strain DH5α (Gibco-BRL) the correct clone was identified by restriction enzyme analysis.

Plasmid pBJ8

The gel purified PvuII restriction fragment containing the origin of replication from pBJ7 was self-ligated using T4 DNA ligase in the presence of 1 mM hexamine cobalt chloride, 25 mM KCI (to encourage self-ligation [Rusche & Howard-Flanders (1985) *Nucleic Acids Research* 13, 1997–2008)]. After transformation into competent *E. coli* strain DH5α (Gibco-BRL) the correct clone was identified by restriction enzyme analysis.

Plasmid pBJ12

Plasmid pUC8α1AT.73 (described in section A1 above) was digested with AccI and HindIII and the resulting fragment containing the alpha$_1$-antitrypsin cDNA minus its polyadenylation signal was end-repaired using Klenow fragment of *E. coli* DNA polymerase in the presence of excess dNTPs. This blunt ended fragment was gel purified and ligated using T4 DNA ligase to gel purified pBJ8 linearised with PvuII. After transformation of competent *E. coli* strain DH5α (Gibco-BRL) the correct clone was identified by restriction enzyme analysis.

Plasmid pBJ1

Plasmid pSS1tgSpS (described in this patent, see A7 below) was digested with BgIII and end-repaired using the Klenow fragment of *E. coli* DNA polymerase in the presence of excess dNTPs. The blunt-ends were modified using HindIII synthetic linkers (New England Biolabs Inc, 32 Tozer Road, Beverly, Mass. 01915-5510, USA) and the resulting fragment self-ligated using T4 DNA ligase in the presence of 1mM hexamine cobalt chloride, 25 mM KCI (to encourage self-ligation [Rusche & Howard-Flanders (1985) *Nucleic Acids Research* 13, 1997-2008)]. After transformation of competent *E. coli* strain DH5α (Gibco-BRL) the correct clone was identified by restriction enzyme analysis.

Plasmid pBJ16 (AATD)

The gel purified HindIII-SphI fragment from pBJ1 and the gel purified SphI-XbaI fragment from pBJ12 were ligated using T4 DNA ligase to gel purified pUC19 (Pharmacia-LKB Biotechnology, Pharmacia House, Midsummer Boulevard, Central Milton Keynes, Bucks, MK9 3HP, UK) digested with HindIII and XbaI. After transformation of competent *E. coli* strain DH5α (Gibco-BRL) the correct clone was identified by restriction enzyme analysis.

Isolation of AAT-D fragment from pBJ16 for microinjection

Plasmid pBJ16 was digested with HindIII and XbaI and the resulting 8.0 kb AATD fragment was isolated from a gel using DE81 paper (Dretzen et al (1981) *Analytical Biochemistry* 112, 285–298). After separation from the DE81 paper the DNA was phenol/chloroform extracted, ethanol precipitated and finally resuspended in TE buffer (10 mM Tris-HCl, 1mM EDTA pH 8) ready for microinjection.

A6 FIXD—Construction of PBJ17

The procedure of Example 1 A5 (construction of AATD) is repeated, except that the DNA sequence encoding the polypeptide of interest encodes Factor IX. A NheI-HindIII fragment comprising 1553 bp of the insert from p5'G3'CVI [see International Patent Application No. WO-A-8800239 (Pharmaceutical Proteins Ltd)] was inserted into the PvuII site of pBJ8 as described above for pBJ12.

A7 DELTA-A2—Construction of pSS1tqXDELTA-AvaII (DELTA A2)

This construct contains the minimum ovine beta-lactoglobulin sequences that have so far been shown in transgenic mice to result in tissue-specific expression of the protein during lactation. The complete sequence of this construct can be found in Harris, Ali, Anderson, Archibald & Clark (1988), *Nucleic Acids Research* 16 (in press).

Plasmid pSS1tgSpS

The gel purified SalI-SphI restriction fragment of approximately 4.2 kb isolated from pSS1tgXS (described in patent WO-A-8800239) was ligated, using T4 DNA ligase, with equimolar amounts of gel purified pPolyI (Lathe, Vilotte & Clark,. 1987, *Gene* 57, 193–201) digested with SalI and SphI. [The vector pPolyI is freely available from Professor R. Lathe, LGME-CNRS and U184 INSERM, 11 rue Humann, 67085 Strasbourg, France.] After transformation of competent *E. coli* strain DH1 (Gibco-BRL) the correct clone was identified by restriction analysis.

Plasmid pSS1tgSpDELTA-AvaII

Plasmid pSS1tgSpS was partially digested with AvaI followed by digestion to completion with SalI. The ends of the resultant DNA fragments were end-repaired using the Klenow fragment of *E. coli* DNA polymerase in the presence of excess dNTPs. After ligation using T4 DNA ligase in the presence of lmM hexamine cobalt chloride, 25 mM KCI [to encourage self-ligation (Rusche & Howard-Flanders (1985) *Nucleic Acids Research* 13, 1997–2008)], the DNA was used to transform competent DHl (Gibco-BRL). The correct AvaI deletion recombinant was confirmed by restriction analysis.

Plasmid pSS1tgXDELTA-AvaII

The gel purified ~800 bp SphI-BgIII fragment from pSS1tgSpDELTA-AvaII; ~6.5 kb SphI-XbaI fragment from pSS1tgXS; and pPolyI digested with BgIII-XbaI were ligated in approximately equimolar ratios u'sing T4 DNA ligase then used to transform competent DH1 (Gibco-BRL). The identity of the correct recombinant was confirmed by restriction analysis.

Isolation of DNA fragment for injection pSS1tgXDELTA-AvaII was digested to completion with BgIII and XbaI to release the ~7.4 kb insert from the vector. The insert was recovered from an agarose gel using DE81 paper (Dretzen et al (1981) *Analytical Biochemistry* 112, 295–298). After separation from the DE81 paper the DNA was phenol/chloroform extracted, ethanol precipitated and resuspended in 100 µl TE ready for microinjection. Alternatively, the insert was recovered from an agarose gel by electroelution onto dialysis membrane (Smith (1980) *Methods in Enzymology* 65, 371–380). After release from the membrane the DNA was phenol/chloroform extracted, ethanol precipitated and resuspended in 100 µl $H_2O$ ready for microinjection.

B. CONSTRUCTION OF TRANSGENIC ANIMALS

Mice

Procedures are similar to those described by Hogan, Costantini and Lacy in "Manipulating the Mouse Embryo: A Laboratory Manual" Cold Spring Harbor Laboratory (1986).

Collection of Fertilised Eggs

Mice used for the collection of fertilised eggs are $F_1$ hybrids between the C57BL/6 and CBA inbred strains of mice. C57BL/6 females and CBA males are obtained from Harlan Olac Ltd (Shaw's Farm, Bicester OX6 OTP, England) and used for the breeding of $F_1$ hybrids. The mice are housed in controlled light conditions (lights on at 03.00 h, lights off at 17.00 h). To induce superovulation, adult female mice are injected with 5 international units of Pregnant Mares Serum Gonadotropin (Cat. No. 4877, Sigma Chemical Company, Poole, Dorset, England) in 0.1 ml of distilled water, at 15.00 h followed 46 to 48 hours later by injection of 5 international units of Human Chorionic Gonadotropin (HCG) (Cat. No. CG-10, Sigma Chemical Company, Poole, Dorset, England) in 0.1 ml of distilled water. Following HCG injection, the females are housed individually with mature C57BL/6 X CBA $F_1$ male mice for mating. The following morning, mated female mice are identified by the presence of a vaginal plug.

Mated females are killed by cervical dislocation. All subsequent procedures are performed taking precautions to avoid bacterial and fungal contamination. Oviducts are excised and placed in M2 culture medium (Hogan, Costantini and Lacy "Manipulating the Mouse Embryo: A Laboratory Manual" Cold Spring Harbor Laboratory (1986) pp254–256). The fertilised eggs are dissected out of the ampullae of the oviducts into M2 containing 300 µg/ml hyaluronidase (Type IV-S, Cat. No. H3884, Sigma Chemical Company, Poole, Dorset, England) to release the cumulus cells surrounding the fertilised eggs. Once the eggs are free of cumulus, they are washed free of hyaluronidase and, until required for injection, are kept at 37° C. either in M2 in a humidified incubator, or in a drop (100–200 µl) of Medium No. 16 (Hogan, Costantini and Lacy "Manipulating the Mouse Embryo: A Laboratory Manual" Cold Spring Harbor Laboratory (1986) pp254–255, and 257), under mineral oil (Cat. No. 400-5, Sigma Chemical Company, Poole, Dorset, England) in an atmosphere of 95% air, 5% $CO_2$.

Injection of DNA

The DNA to be injected is diluted to approximately 1.5 µg/ml in AnalaR water (Cat. No. 10292 3C, BDH Chemicals, Burnfield Avenue, Glasgow G46 7TP, Scotland), previously sterilised by filtration through a 0.2 µm pore size filter (Cat. No. SM 16534, Sartorious, 18 Avenue Road, Belmont, Surrey SM2 6JD, England). All micropipette tips and microcentrifuge tubes used to handle the DNA and diluent are rinsed in 0.2 µm-filtered water, to remove particulate matter which could potentially block the injection pipette. The diluted DNA is centrifuged at 12000×g for at least 15 minutes to allow any particulate matter to sediment or float; a 20 µl aliquot is removed from just below the surface and used to fill the injection pipettes.

Injection pipettes are prepared on the same day they are to be used, from 15 cm long, 1.0 mm outside diameter, thin wall, borosilicate glass capillaries, with filament (Cat. No.' GC100TF-15; Clark Electromedical Instruments, PO Box 8, Pangbourne, Reading, RG8 7HU, England), by using a microelectrode puller (Campden Instruments, 186 Campden Hill Road, London, England). DNA (approximately 1 µl) is introduced into the injection pipettes at the broad end; it is carried to the tip by capillary action along the filament. To prevent evaporation of water from the DNA solution, approximately 20 µl Fluorinert FC77 (Cat. No. F4758, Sigma Chemical Company, Poole, Dorset, England) is laid over the DNA solution. The filled injection pipettes are stored at 4° C. until required.

The holding pipette (used to immobilise the eggs for microinjection) is prepared from 10 cm long, 1.0 mm outside diameter, borosilicate glass capillaries (cat. No. GC100-10; Clark Electromedical Instruments, PO Box 8, Pangbourne, Reading RG8 7HU, England). The glass is heated over a small flame and pulled by hand to give a 2–4 cm long section with a diameter of 80–120 µm. Bends are introduced into the pipette, the glass is broken and- the tip is polished using a microforge (Research Instruments, Kernick Road, Penryn TR10 9DQ, England).

A cover slip chamber is constructed in which to micromanipulate the eggs. The base of the cover-slip chamber is a 26×76× (1–1.2)mm microscope slide (Cat. No. ML330-12, A and J Beveridge Ltd, 5 Bonnington Road Lane, Edinburgh EH6 5BP, Scotland) siliconised. with 2% dimethyldichlorosilane (Cat. No. 33164 4V, BDH Chemicals, Burnfield Avenue, Glasgow G46 7TP, Scotland) according to the manufacturer's instructions; two glass supports (25×3×1 mm, cut from microscope slides) are -fixed onto the slide with high vacuum silicone grease (Cat. No. 33135 3N, BDH Chemicals, Burnfield Avenue, Glasgow G46 7TP, Scotland) parallel to and approximately 2 mm from the long sides of the slide, half way along the length of the slide. A further two glass supports are fixed on top of the first pair, and the top surface is smeared with silicone grease. 300 $\mu$l of medium M2 are pipetted into the space between the supports, and a 22×22 mm cover-slip (Cat. No. ML544-20, A and J Beveridge Ltd, 5 Bonnington Road Lane, Edinburgh EH6 5BP, Scotland) is lowered onto the supports, a seal being formed by the grease. Dow-Corning fluid (50 cs) (Cat. No. 63006 4V, BDH Chemicals, Burnfield Avenue, Glasgow G46 7TP, Scotland) is pipetted into the open ends of the chamber, to cover the medium.

Batches of eggs (30 to 100) are placed into a cover-slip chamber for manipulation. The chamber is mounted on the microscope (Diaphot, Nikon (UK) Ltd, Haybrooke, Telford, Shropshire, England) which has 4× bright field, 10× phase contrast and 40× differential interference contrast (DIC) objectives, and 10× eyepieces. Mechanical micromanipulators (Cat. Nos. 520 137 and 520 138, E. Leitz (Instruments) Ltd, 48 Park Street, Luton, England) are mounted adjacent to the microscope and are used to control the positions of the holding and injection pipettes.

The holding pipette and DNA-containing injection pipette are mounted in modified instrument tubes (Cat. No. 520 145, E. Leitz' (Instruments) Ltd, 48 Park Street, Luton, England) which are in turn mounted onto the micromanipulators via single unit (Cat. Nd. 520 142, E. Leitz (Instruments) Ltd, 48 Park Street, Luton, England) and double unit (Cat. No. 520 143, E. Leitz (In struments) Ltd, 48 Park Street, Luton, England) instrument holders, respectively. The instrument tubes are modified by gluing onto Clay Adams "Intramedic" adapters (2.0–3.5 mm tubing to female Luer, Cat. No. 7543D, Arnold R. Horwell Ltd, 2 Grangeway, Kilburn High Road, London NW6 2BP, England), which are used to connect the instrument tubes to approximately 2 metres of polythene.tubing (1.57 mm inside diameter, 2.9 mm outside diameter, Cat. No. F21852-0062, R.B. Radley & Co, Ltd, London Road, Sawbridgeworth, Herts CM21 9JH, England), further "Intramedic" adapters are connected to the other ends of the polythene tubing to facilitate connection to the syringes used to control the holding and injection pipettes.

Injection is controlled using a 20 ml or a 100 ml glass syringe (Cat. Nos. M611/20 and M611/31, Fisons, Bishop Meadow Road, Loughborough LE11 ORG, England), the plunger of which is lightly greased with high vacuum silicone grease (Cat. No. 33135 3N, BDH Chemicals, Burnfield Avenue, Glasgow G46 7TP, Scotland).

Holding of eggs is controlled with an Agla micrometer syringe (Cat. No. MS01, Wellcome Diagnostics, Temple Hill, Dartford DA1 SAH, England), which is fitted with a light spring around the plunger. The Agla syringe is connected via a 3-way stopcock (Cat. No. SYA-580-L), Gallenkamp, Belton Road West, Loughborough LE11 OTR, England), to the "Intramedic" adapter, the third port of the stopcock is connected to a reservoir of Fluorinert FC77 (Cat. No. F 4758, Sigma Chemical Company, Poole, Dorset, England), which fills the Agla syringe, polythene tubing, instrument tube and holding pipette.

The tip of the injection pipette is broken off against the holding pipette, to increase the tip diameter to: a size which allows free passage of the DNA solution and which is small enough to allow injection without lethal damage to the eggs ($\leq 1$ $\mu$m). The flow of DNA through the pipette tip is checked by viewing under phase contrast conditions whilst pressure is applied to the injection syringe (the DNA solution will appear as a bright plume emerging from the tip of the pipette).

One by one, fertilised eggs are picked up on the holding pipette, and one or both pronuclei brought into the same focus as the injection pipette (using the 40× objective and DIC conditions; the correction ring on the objective is adjusted for optimum resolution). The injection pipette is inserted into one of the pronuclei, avoiding the nucleoli, pressure is applied to the injection syringe and once swelling of the pronucleus is observed, pressure is released and the injection pipette is immediately withdrawn. When pipettes block, the blockage may be cleared by application of high pressure on the injection syringe or by breaking off a further portion of the tip. If the blockage cannot be cleared, or if the pipette tip becomes dirty, the pipette is replaced.

After injection, the eggs are cultured overnight in medium No. 16 under oil in an atmosphere of 5% $CO_2$. Eggs which cleave to two cells during overnight culture are implanted into pseudopregnant foster mothers.

Random-bred albino (MFl, Harlan Olac Ltd, Shaw's Farm, Bicester, OX6 OTP, England) female mice are mated with vasectomised (Hogan, Costantini and Lacy, "Manipulating the Mouse Embryo: A Laboratory Manual" Cold Spring Harbor Laboratory (1986); Rafferty, "Methods in experimental embryology of the mouse", The Johns Hopkins Press, Baltimore, USA (1970)) MF1 male mice. The matings are performed one day later than those of the superovulated egg donors. MF1 females which have a detectable vaginal plug the following morning are used as foster mothers. The ideal weight of foster mothers is 25 to 30 g. Each foster mother is anaesthetised by intraperitoneal injection of Hypnorm/Hypnovel (10 $\mu$l/g body weight) at $\frac{2}{3}$ the concentration recommended by Flecknell (Veterinary Record, 113, 574) (Hypnorm: Crown Chemical Co, Ltd, Lamberhurst, Kent TN3 8DJ, England; Hypnovel: Roche Products Ltd, PO Box 8, Welwyn Garden City, Herts AL7 3AY, England) and 20 to 30 2-cell eggs are transferred into one oviduct by the method described by Hogan, Costantini and Lacy ("Manipulating the Mouse Embryo: A Laboratory Manual" Cold Spring Harbor Laboratory (1986)). As an option, to minimise bleeding from the ovearian bursa, 2 $\mu$l of 0.01% (w:v) epinephrine bitartrate (Cat. No. E4375, Sigma Chemical Company, Poole, Dorset, England) dissolved in distilled water is applied to the bursa a few minutes before tearing it. Foster mothers are allowed to deliver their offspring naturally unless they have not done so by 19 days after egg transfer, in which case the pups are delivered by hysterectomy, and are fostered. Following normal mouse husbandry, the pups are weaned at 3 to 4 weeks of age and housed with other mice of the same sex only.

Transgenic female mice may be used for the breeding of subsequent generations of transgenic mice by standard procedures and/or for the collection of milk and RNA. Transgenic male mice are used to breed subsequent generations of transgenic mice by standard procedures. Transgenic mice of subsequent generations are identified by analysis of DNA prepared from tails, as described below.

Sheep

The generation of transgenic sheep is described in detail in International Patent Application No. WO-A-8800239 (Pharmaceutical Proteins Ltd) and by Simons, Wilmut, Clark, Archibald, Bishop & Lathe (1988) Biotechnology 6, 179–183.

C. IDENTIFICATION OF TRANSGENIC INDIVIDUALS

Mice

When the pups are at least 4 weeks of age, a biopsy of tail is taken for the preparation of DNA. The pups are anaesthetised by intraperitoneal injection of Hypnorm/Hypnovel (10 μl/g body weight) at ½ the concentration recommended by Flecknell (Veterinary Record, 113, 574). Once anaesthetised, a portion of tail (1to 2 cm) is removed by cutting with a scalpel which has been heated in a Bunsen flame; the hot blade cauterises the wound and prevents bleeding.

The tail segments are digested with proteinase K 200 μg/ml (Sigma) in tail buffer [0.3 M NaAcetate (not titrated), 10 MM Tris-HCl pH 7.9, 1 mM EDTA pH 8.0, 1% SDS] overnight with shaking at 37° C. The following day the digests are vortexed briefly to disaggregate the debris. Aliquots of digested tail are phenol/chloroform extracted once, chloroform extracted once and then DNA is recovered by precipitation with an equal volume of isopropanol.

'Tail DNA' is digested with restriction enzyme(s), and subjected to agarose gel electrophoresis. The separated DNA is then 'Southern' blotted to Hybond™ N (Amersham) nylon membranes as described in the Amersham Handbook 'Membrane transfer and detection methods' (P1/162/86/8 published by Amersham International plc, PO Box 16, Amersham, Buckinghamshire HP7 9LL, UK). DNA bound to the membranes is probed by hybridisation to appropriate $^{32}$P labelled DNA sequences (eg the construct DNAs). The DNA probes are labelled with $^{32}$P by nick-translation as described in 'Molecular Cloning: a Laboratory Manual' (1982) by Maniatis, Fritsch and Sambrook, published by Cold Spring Harbor Laboratory, Box 100, Cold Spring Harbor, USA. Alternatively DNA probes are labelled using random primers by the method described by Feinberg and Vogelstein (1984) Analytical Biochemistry 137, 266–267. Briefly: The plasmid or phage is cleaved with the appropriate restriction enzymes and the desired fragment isolated from an agarose gel. The labelling reaction is carried out at room temperature by adding the following reagents in order: H$_2$O, 6 μl OLB*, 1.2 μl BSA, DNA (max. 25 ng), 4 μl $^{32}$P labelled dCTP (PB10205, Amersham plc, Amersham UK), 1 μl (1 unit) Klenow Polymerase (BCL) to a final volume of 30 μl.

*OLB comprises solution A: 625 μl 2M Tris, pH 8.0+25 μl SM. MgC12+350 μl H$_2$O+18 μl 2-mercaptoethanol (Sigma); solution B, 2M HEPES (Sigma), titrated to pH 6.6 with NaOH; solution C, Hexa deoxyribonucleotides (Pharmacia-LKB Biotechnology Cat. No. 27-2166-01). The labelling reaction is allowed to run overnight and then the reaction stopped by the addition of 70 μl stop solution (20 mM Nacl, 20 mM Tris pH 7.5, 2mM EDTA, 0.25% SDS, 1 μM dCTP). Incorporation is assessed by TCA precipitation and counting Cerenkov emission.

Hybridisations are carried out in sealed plastic bags by a modification of the procedure described by Church and Gilbert (1984). Proceedings of the National Academy of Sciences (USA) 81, 1991–1995. Briefly: the probe is used at a concentration of 1;5x10$^6$ Cerenkov counts/ml of hybridisation buffer (HB: 0.5M sodium phosphate pH 7.2, 7% SDS, 1 mM EDTA). Firstly, the membrane is prehybridised for 5 minutes in HB (15ml of buffer per 20 cm$^2$ membrane) in the plastic bag at 65° C. The probe is denatured by boiling and added to the same volume of fresh HB. The plastic bag is cut open and the prehybridisation solution drained and then the HB+probe added and the bag re-sealed. The bag and contents are incubated overnight on a rotary shaker at 65° C. After hybridisation the membrane is washed in 40 mM sodium phosphate, 1% SDS and 1 mM EDTA three times for ten minutes at 65° C. and then a final wash is carried out for 15–30 minutes at this temperature. Washing is monitored with a hand-held Geiger counter. The stringency of the washings may be adjusted according to the particular needs of the experiment. After the last wash the membrane is blotted dry and then placed on a dry piece of Whatman filter paper and wrapped in Saran-wrap. The membrane is exposed to X-ray film (Agfa CURIX RP-1) using an X-ray cassette at −70° C. for one or more days.

By comparison with known amounts of construct DNA treated in the same manner DNA from transgenic individuals can be identified and the number of copies of the construct DNA which have been integrated into the genome can be estimated.

The same methods are used to identify transgenic offspring of the founder transgenic individuals.

Sheep

The identification of transgenic sheep is described in detail in International Patent Application No. WO-A-8800239 (Pharmaceutical Proteins Ltd).

D. ANALYSIS OF EXPRESSION—METHODS

Collection of Mouse Milk

Female mice (at least 7 weeks of age) are housed individually with adult male mice for mating. After 17 days, the male mice are removed from the cage and the female mice are observed daily for the birth of offspring. Milk and/or RNA are collected 11 days after parturition.

For the collection of milk, the pups are separated from the lactating female mice to allow the build-up of milk in the mammary glands. After at least 3 hours, 0.3 international units of oxytocin (Sigma, Cat. No. 0 4250) in 0.1 ml of distilled water are administered by intraperitoneal injection, followed after 10 minutes by intraperitoneal injection of Hypnorm/Hypnovel anaesthetic (10 μl/g body weight) at ⅔ the concentration recommended by Flecknell (Veterinary Record, 113, 574). When fully anaesthetised, the mammary glands are massaged to expel milk, which is collected in 50 μl capillary tubes (Drummond Microcaps, Cat. No. PP600-78, A and J Beveridge Ltd, 5 Bonnington Road Lane, Edinburgh EH6 5BP, Scotland).

Mouse milk is diluted 1:5 in distilled water and centrifuged in an Eppendorf 5415 centrifuge (BDH) to remove fat. To make whey, 1.0 M HCl was added to give a final pH of 4.5, thus precipitating the caseins which were then removed by centrifugation in an Eppendorf 5415 centrifuge. Diluted milk or whey samples were solubilised by boiling in loading buffer prior to discontinuous SDS polyacrylamide gel electrophoresis (Laemmli (1970) *Nature* 277, 680–684) and immunoblotting analysis (Khyse-Anderson (1984) *Journal of Biochemical and Biophysical Methods* 10, 203–209). Human alpha$_1$-antitrypsin (AAT) was identified on immunoblot filters by using goat-anti-AT serum [Protein Reference Unit, Royal Hallamshire Hospital, Sheffield S10 2JF] and anti-sheep/goat IgG serum conjugated to horseradish peroxidase [Scottish Antibody Production Unit, Glasgow and West of Scotland Blood Transfusion Service, Law Hospital, Carluke, Lanarkshire ML8 5ES].

Amounts of human alpha$_1$-antitrypsin (AAT) in mouse milk were measured by using LC-Partigen radial immunodiffusion plates [Behring Diagnostics, Hoescht UK Ltd, 50 Salisbury Road, Hounslow, Middlesex TW4 6JH]. The radial immunodiffusion (RID) method, which is designed to detect AAT in body fluids in the concentration range 8–125 μg/ml, was carried out according to the manufacturers instructions. Three dilutions of standard human serum [LC-V, Behring Diagnostics] were prepared in phosphate buffered saline (PBS) to give AAT concentrations which fell within the detection range for the assay.

Test milk samples were diluted 1:5 in distilled water and defatted by spinning briefly in an Eppendorf 5415 centrifuge (BDH). The following control experiment was carried out in order to assess the effect of the milk environment on the detection of AAT (the method is primarily designed for measuring AAT in blood serum). Milk samples from non-transgenic mice were assayed with and without defined amounts of added AAT. Samples (20 µl) were loaded into the wells and the plates left open for 10–20 minutes. The plates were then sealed with the plastic lids provided and left to stand at room temperature. The diameters of the precipitation zones were measured after a diffusion time of 2–3 days, using a low power binocular microscope fitted with a lens graticule. At least three independent readings were recorded and the average measurement (mm) calculated and squared ($mm^2$). A calibration curve plotting zone measurement squared against AAT concentration was constructed using the values obtained with the dilutions of standard human serum. This linear graph was used to calculate the AAT concentrations in the test samples.

Preparation of RNA

RNA may be prepared from mice immediately after milking or from mice which have not been milked. The lactating female mouse is killed by cervical dislocation and tissues excised, taking care to avoid cross-contamination of samples. The procedure is based on the protocol described by Chirgwin, Przybyla, MacDonald and Rutter (1979) Biochemistry 18, 5294–5299.

The tissue of interest is dissected and placed in 4 ml of a 4 M solution of Guanadine Thiocyanate in a sterile 30 ml disposable plastic tube. The tissue is homogenised using an Ultra-Turrax$^R$ homogeniser at full speed for 30–45 seconds at room temperature. The homogenate is layered onto a 1.2 ml, 5.7 M CsCl solution in a 5 ml polyallomer ultracentrifuge tube (Sorvall Cat. 03127; Du Pont (UK) Ltd, Wedgwood Way, Stevenage, Hertfordshire SG1 4QN, UK). The RNA is pelleted through the cushion of CsCl by centrifuging at 36,000 rpm for 12 hrs at 20° C. using a Sorvall AH650 or Beckman SW50.1 swing-out rotor in a Beckman L80 ultracentrifuge (Beckman Instruments (UK) Ltd, Progress Road, Sands Industrial Estate, High Wycombe, Bucks HP12 4JL, UK). After centrifugation the supernatant is removed with sterile disposable plastic 5 ml pipettes and the tube is then very carefully drained. The RNA which should be visible as an opalescent pellet at the bottom of the tube is resuspended in 2 ml of 7.5 M Guanidine Hydrochloride with vigorous vortexing. Resuspension may take 15 minutes or longer. The preparation is transferred to a 15 or 30 ml heat-sterilised Corex™ (Du Pont) centrifuge tube and precipitated by the addition of 50 µl of 1M acetic acid and 1 ml of 100% ethanol and incubation overnight at −20° C. The RNA is pelleted using a Sorvall SS34 rotor (Du Pont) in a Sorvall RCB5 refrigerated centrifuge (Du Pont) at 10,000 rpm for 10 minutes at 2° C. The RNA pellet is resuspended in 2 ml of diethylpyrocarbonate (Sigma) (DEPC)-treated distilled water by vortexing. The RNA is re-precipitated by the addition of 600 µl of 1M sodium acetate (DEPC-treated) and 3 volumes of 100% ethanol, resuspended in DEPC treated water and again precipitated. After the second precipitation from DEPC water the RNA pellet is resuspended in DEPC water to the desired final volume (usually 100 µl–500 µl). The concentration of RNA is determined spectrophotometrically ($OD_{260nm}=1$ corresponds to 40 µg/ml). RNA preparations are stored frozen at −70° C.

Analysis of RNA

The expression of the introduced transgene was investigated in a number of different tissues by 'Northern' blotting of the RNA samples prepared by the procedure described above. Aliquots (10 µg–20 µg) of total RNA were denatured and separated in denaturing MOPS/formaldehyde (1–1.5%) agarose gels and transferred to Hybond™ N (Amersham) nylon membranes as described in the Amersham Handbook 'Membrane transfer and detection methods' (PI/162/86/8 published by Amersham International plc, PO Box 16, Amersham, Buckinghamshire HP7 9LL, UK). The RNA bound to the membranes is probed by hybridisation to appropriate $^{32}P$ labelled DNA sequences (eg encoding BLG, FIX or AAT). The labelling and hybridisation procedures are described in section 1C above.

In some cases RNA transcripts were detected using an RNase protection assay. This allows the determination of the transcriptional start point of the gene. The procedure essentially follows that described by Melton, Krieg, Rebagliati, Maniatis, Zinn and Green (1984) Nucleic Acids Research 18, 7035–7054. For example, for FIX a 145 bp SphI-EcoRV fragment from pS1tgXSFIX (WO-A-8800239) which spans the 5' fusion point of BLG and FIX was cloned into SphI-SmaI cleaved pGEM4 (ProMega Biotec, 2800 South Fish Hatchery Road, Madison, Wis. 53791-9889, USA). A 192 nucleotide long $^{32}P$ labelled, antisense RNA transcript was generated using SP6 polymerase was used in the RNase protection assays. After annealing the 'samples were digested with RNAase A (BCL) (40 µg/ml) and RNase Tl(BCL) (2 µg/ml) at 37° C. for one hour. Phenol/Chloroform purified samples were electrophoresed on 8% polyacrylamide/urea sequencing gels.

EXAMPLE 2

Expression of the AATB Construct in Transgenic Mice

The efficient expression of a human plasma protein.in the milk of transgenic mice is exemplified by construct AATB. The details of the construction of AATB are given in Example 1. Briefly AATB contains the genomic sequences for the human (liver) alpha$_1$-antitrypsin gene minus intron 1, fused to the promoter of the ovine beta-lactoglobulin gene. The fusion point is in the 5'-untranslated region of the BLG gene. It was anticipated that the presence of the AAT introns would enhance the levels of expression of the construct. The large first AAT intron (ca. 5 kb) was omitted in order to facilitate the DNA manipulation of the construct and to determine whether all the AAT introns were required for efficient expression.

Unless otherwise stated the analyses of expression are tabulated. '+' indicates expression as determined by the presence of the appropriate mRNA transcript (detected by Northern blotting) or protein (as detected by radial immunodiffusion (RID) or immunoblotting (Western blotting)). '−' indicates that the expression was not detected.

Transgenic Mice Carrying the AATB Construct

The AATB construct described in Example 1 was used to generate transgenic mice by the methods outlined in Example 1. AATB construct DNA was microinjected into fertilised mouse eggs on 7 occasions between August 1987 and June 1988. A total of 993 eggs were injected of which 747 were transferred to recipient pseudo-pregnant mice. A total of 122 pups were weaned. Analysis of DNA prepared from tail biopsies, as described in Example 1C, revealed that of these 122 generation zero (G0) pups 21 carried the AATB construct as a transgene (see Table 1). These transgenic mice had between 1 and >20 copies of the AATB construct integrated into their genome.

The following policy was adopted for the study of the expression of the AATB transgene. Where a founder transgenic G0 individual was male, he was mated to non-transgenic females to generate G1 offspring. Tail DNAs from G1 individuals were examined to determine whether they had inherited the transgene. Female transgenic G1 mice were used for the analysis of expression of the AATB transgene by the methods described in Example 1D. Where a founder transgenic G0 individual was female she was used directly for the analysis of expression as described in Example 1D. The adoption of this policy meant that lines of mice were only established where the founder G0 animal was male. The transmission of the transgenes to subsequent generations has also only been determined where the founder G0 mouse was male. Transmission data for four AATB G0 males is given in Table 1.

TABLE 1

Mice carrying the AATB construct as a transgene.

| Animal ID | Sex | Copy Number | Transmission data | |
|---|---|---|---|---|
| | | | No. of offspring/ | No. transgenic |
| AATB15 | male | 2–5 | 25 | 8 |
| AATB17 | male | 10–15 | 26 | 16 |
| AATB26 | male | >20 | 34 | 5 |
| AATB28 | male | 2–5 | 22 | 12 |
| AATB44 | female | 15 | | |
| AATB45 | female | 1–2 | | |
| AATB65 | female | 2–3 | | |
| AATB69 | female | 1–2 | | |
| AATB105 | female | 20 | | |

Analysis of Expression

Fifteen G1 females have been examined for expression of -the AATB transgene, 8 by protein analysis of milk and 7 by RNA analysis by the methods described in Example 1. A further 5 G0 females have been examined by both protein analysis of milk and RNA analysis. A total of 9 different transgenic mice or mouse-lines were examined.

RNA Analysis

Figure 11:
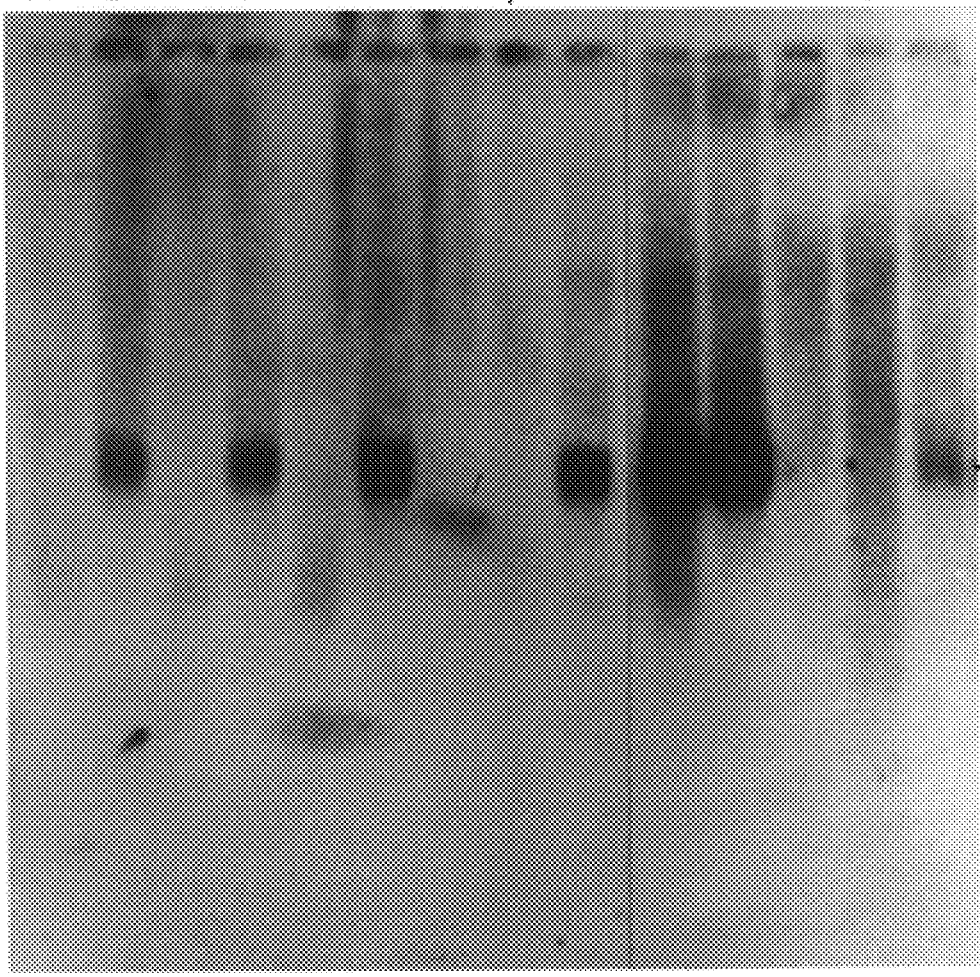
FIG. 11 shows a Northern blot giving the results of Example 2.

RNAs isolated from the following tissues were examined for the presence of AATB transcripts—mammary gland, liver, kidney, spleen, salivary gland and heart. Total RNA samples (10 μg) from these tissues were analysed by Northern blotting. A representative Northern blot is presented as FIG. 11 [Lanes 1 & 2, and 3 & 4 contain mammary (M) and liver (L) samples from control mice; lanes 5–9, AATB26.1 mammary (M), liver (L), kidney (K), spleen (Sp) and salivary (Sa) RNA samples; lanes 10–14, AATB17.3 mammary (M), liver (L), kidney (K), spleen (Sp) and salivary (Sa) RNA samples. The AAT transcript of approximately 1400 nucleotides is arrowed]. The human AAT cDNA probe, p8α1ppg, cross-hybridises with endogenous mouse AAT transcripts in liver RNA samples. The presence of AAT transcripts in salivary samples from AATB26.1 and AATB17.3 do not result from contamination with liver or mammary material as proved by re-probing the filters with liver-specific and salivary-specific probes. The results of this analysis are summarised in Table 2.

TABLE 2

Summary of RNA analysis for AATB transgenic mice.

| | | Tissue (presence/absence of AATB transcripts) | | | | | |
|---|---|---|---|---|---|---|---|
| Animal ID | Generation | Mam. | Liver | Kid. | Spl. | Saliv. | Heart |
| AATB15.2 | G1 | +* | ? | – | – | – | – |
| AATB15.13 | G1 | – | ? | – | – | – | NT |
| AATB17.3 | G1 | + | ? | – | – | + | NT |
| AATB17.20 | G1 | + | – | – | – | + | NT |
| AATB26.1 | G1 | – | – | – | – | + | NT |
| AATB26.28 | G1 | – | ? | – | – | + | – |
| AATB28.3 | G1 | – | ? | – | – | – | NT |
| AATB28.21 | G1 | – | ? | – | – | – | NT |
| AATB44 | G0 | + | ? | – | – | – | – |
| AATB45 | G0 | + | ? | – | – | – | – |
| AATB65 | G0 | + | ? | – | – | – | – |
| AATB69 | G0 | + | ? | – | – | – | – |
| AATB105 | G0 | – | ? | – | – | + | – |

[Mam. = mammary gland; Kid. = kidney; Spl. = spleen; Saliv. = salivary gland; nd = not detected; NT = not tested]
*presence only detected in poly A+ RNA
? background from endogenous mouse AAT transcripts in liver precluded an unambiguous determination of whether there were AATB transcripts present.

Figure 12:
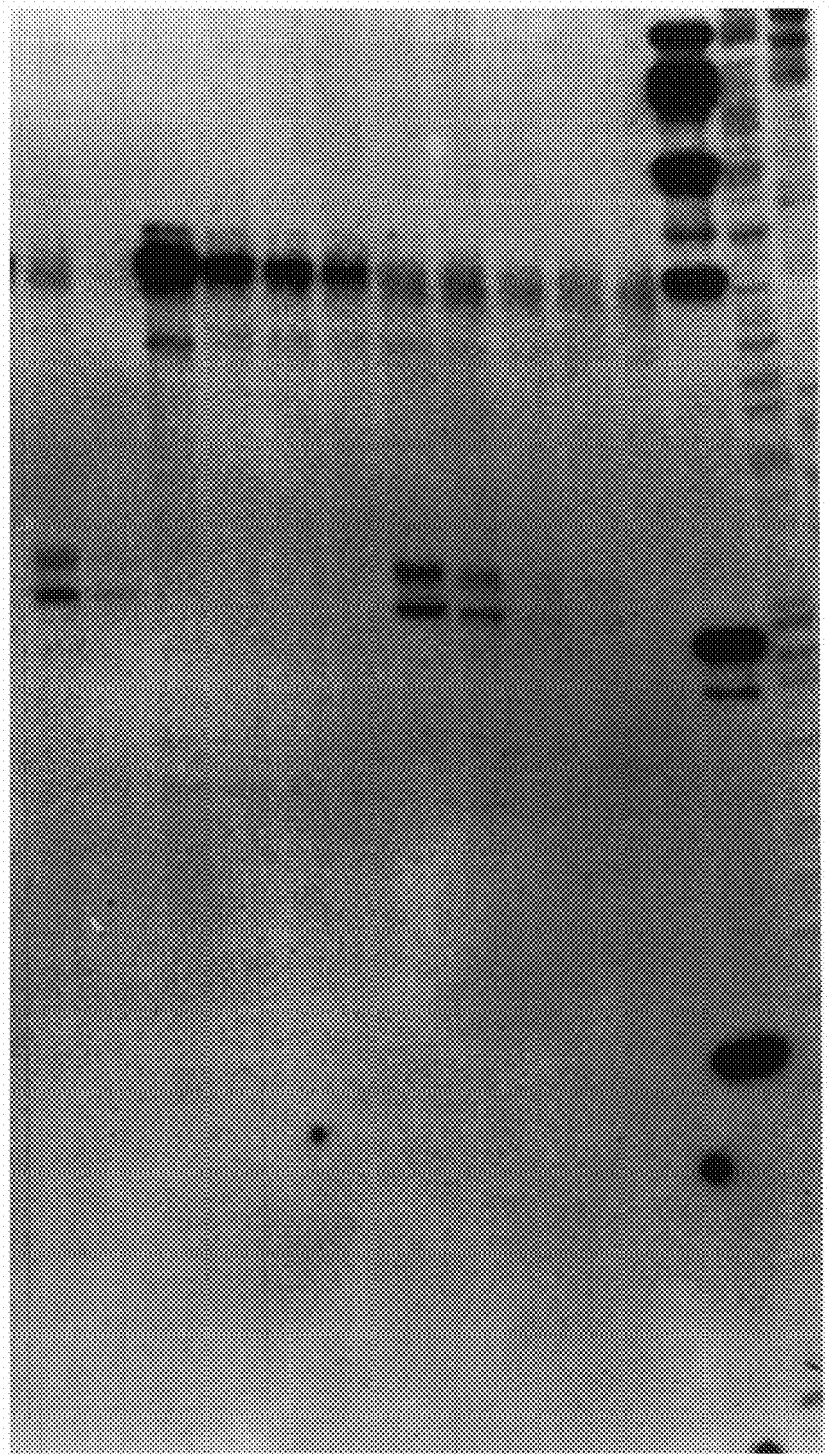
FIG. 12 shows an RNase protection gel, referred to in Example 2.

In order to confirm that the transcripts observed were being initiated at the beta-lactoglobulin start site in the AATB constructs, RNAs isolated from the mammary gland of mouse AATB17.20 and from the salivary gland of mouse AATB26.1 were examined by an RNase protection assay as described in Example 1D. RNAs isolated from the liver (AATB17.20 & AATB26.1) and from the mammary gland (AATB26.1) of these mice were also examined by RNAse protection, as were RNAs from non-transgenic liver, mammary gland and salivary gland. The anti-sense probe was produced by transcribing a pGEM vector (Promega Biotec, 2800 South Fish Hatchery Road, Madison, Wis. 53791–9889) containing a 155 bp SphI-BamHI fragment derived from the 5' end of the AATA construct. This 155 bp fragment is identical to that found in AATB (see pIII-ISpB, Example 1A). Annealing was carried out under standard conditions and the hydrolysis of single-stranded RNA performed with RNaseA and RNaseTl(BCL). A sense transcript was also transcribed and various amounts of this transcript included along with 20 μg samples of control RNA to provide an estimation of steady state mRNA levels. A representative RNase protection gel is shown in FIG. 12 [Lanes 1 & 2, AATB17.20 20 μg and 10 μg total mammary RNA; lanes 3, 4, 5 & 6, 1000 pg, 200 pg, 100 pg & 50 pg of control sense transcript; lanes 7 & 8, AATB26.1 20 μg & 10 μg total salivary RNA; lanes 9, 10 & 11, 5 μg aliquots of mammary polyA+ RNA from AATB15.2, AATA5.20 and AATA31; lane M HaeII digested ΦX174 DNA marker track]. The RNase protection assay confirmed that the beta-lactoglobulin transcription start site was being used as predicted in the mammary tissue of line AATB17 and in the salivary tissue of line.AATB26. The absence of AATB transcripts in the liver of AATB17.20 and in the liver and mammary gland of AATB26.1 were also confirmed by RNase protection assays.

Protein Analysis of Milk

Figure 13:
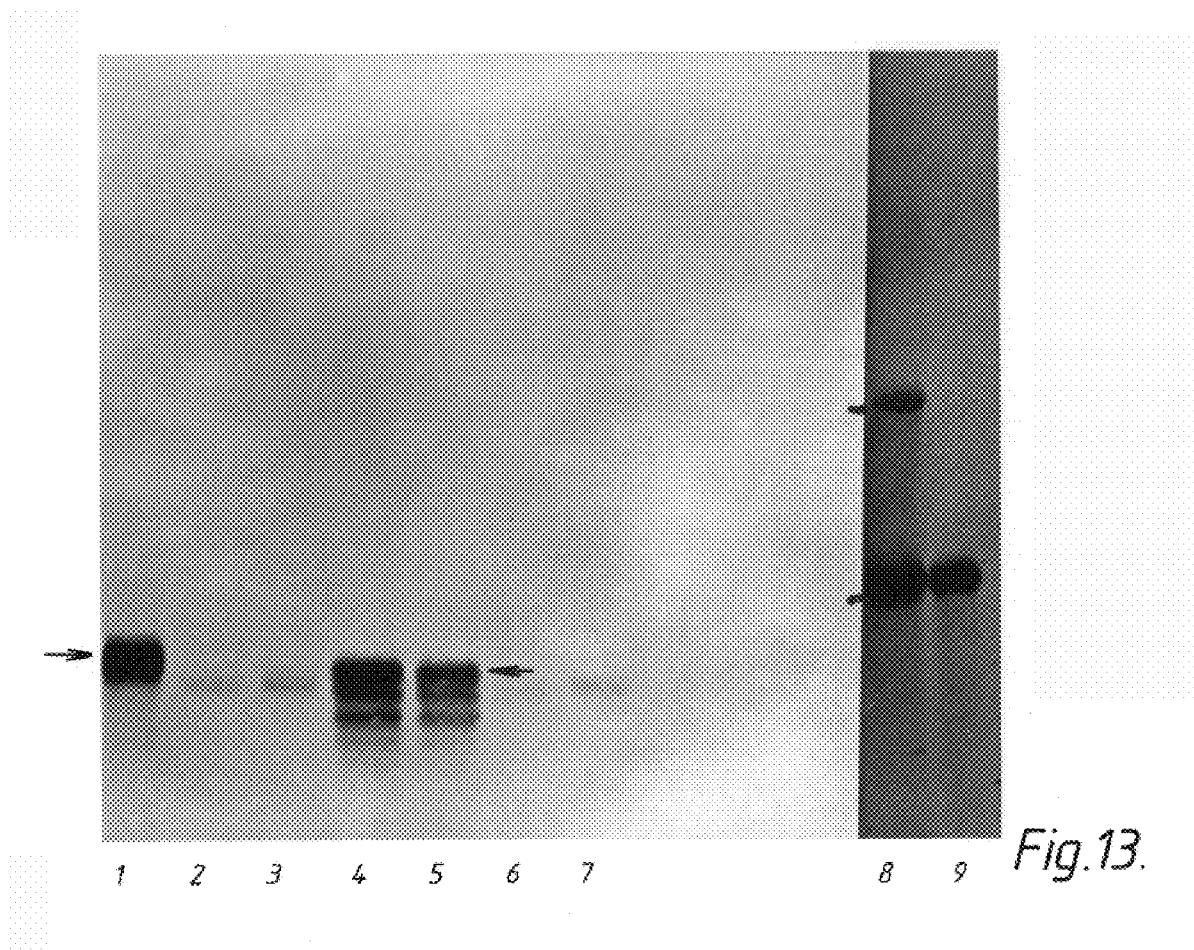
FIG. 13 shows an Immuno blot of diluted milk samples from transgenic and normal mice, referred to in Example 2.

Milk samples from 8 G1 females and from 5 G0 females were assayed for the presence of human alpha$_1$-antitrypsin by the immunoblotting methods described in Example 1D. The results of this analysis are summarised in Table 3. A representative immunoblot of diluted milk samples from transgenic and normal mice is shown as FIG. 13 [lanes 1, pooled human serum; 2, control mouse milk; 3, AATB 15.10 milk; 4, AATB 17.24 milk; 5, AATB 17.23 milk; 6, AATB 15.20 milk; 7, control mouse milk; 8 & 9, marker proteins]. The human AAT (arrowed) is clearly evident in preparations from mice AATB17.23 and AATB17.24 and just about visible in milk from mouse AATB15.10]. Cross reaction of the anti-human sera to endogenous mouse AAT (which migrates slightly faster than its human counterpart) is also evident.

Amounts of human $alpha_1$-antitrypsin in transgenic mouse milk were estimated using LC-Partigen radial immunodiffusion plates [RID] [Behring Diagnostics, Hoescht UK Ltd, 50 Salisbury Road, Hounslow, Middlesex TW4 6JH] as described in Example 1D (see Table 3). Normal mouse milk samples with and without human $alpha_1$-antitrypsin were included as controls.

TABLE 3

| Animal ID | Generation | Immunoblot presence/absence | RID protein mg/ml |
|---|---|---|---|
| AATB15.10 | G1 | + | NT |
| AATB15.20 | G1 | − | NT |
| AATB17.23 | G1 | + | 0.448 |
| AATB17.24 | G1 | + | 0.533 |
| AATB26.14 | G1 | − | NT |
| AATB26.28 | G1 | − | NT |
| AATB28.11 | G1 | − | NT |
| AATB28.14 | G1 | − | NT |
| AATB44 | G0 | + | 0.87 |
| AATB45 | G0 | + | 0.088 |
| AATB65 | G0 | + | 0.091 |
| AATB69 | G0 | + | 0.465 |
| AATB105 | G0 | − | − |

[NT = not tested]

Of the nine different AATB transgenic mice or mouse-lines examined, five efficiently directed expression of human $alpha_1$-antitrypsin in milk. A sixth line (AATB15) also exhibited mammary expression, but at lower levels. This analysis proves that the AATB construct contains sufficient information to direct efficient expression of human $alpha_1$-antitrypsin in the mammary glands of transgenic mice. There appears to be some relaxation of the tissue-specificity of the BLG promoter such as to allow it to function in salivary gland as well as in the mammary gland. The first intron of the AAT gene is not necessary for efficient expression of the hybrid gene AATB. The introns and 3' flanking sequences of the BLG gene are evidently not essential for efficient mammary gland expression from the BLG promoter. The 5' flanking sequences of the BLG gene from SalI through SphI to the PvuII site in the 5'-untranslated of the BLG gene are sufficient to direct the efficient mammary expression of a heterologous gene as exemplified by AAT.

EXAMPLE 3

Comparative Expression of BLG Constructs

The efficient expression of a human plasma protein in the milk of transgenic mice is exemplified by construct AATB. In this section the expression analyses of different constructs encoding a human plasma protein, either FIX or AAT, are given. The details of their constructions are given in Example 1A. Expression analyses of two configurations of the BLG gene are also given and serve to further define the BLG sequences that may be required for expression in the mammary gland. Unless otherwise stated the analyses of expression are tabulated. '+' indicates expression as determined by the presence of the appropriate mRNA transcript (detected by Northern blotting) or protein (as detected by radioimmunoassay (RIA) radial-immunodiffusion (RID) Coomassie blue staining or Western blotting. '−' indicates that expression was not detected.

FIXA:

Construction and expression of this construct; is described in detail in WO-A-8800239 (designated pSS1tgXS-FIX or pSS1tgXS-TARG). It comprises cDNA sequences encoding human blood clotting factor IX (FIX) inserted into the first exon of the BLG gene. Transgenic sheep have been produced which carry this construct and these have been analysed for the expression of human FIX by Northern blotting of mammary RNA and radioimmunoassays of milk:

| Sheep | Description | RNA | FIX Protein (iu*/1) |
|---|---|---|---|
| 6LL240 | G0 female | + | +: 4.7$^a$, 8.0$^b$ |
| 6LL231 | G0 female | + | +: 4.0a, 4.3b |
| 7R45 | G1 female@ | + | +:/5.7b |
| 7R39 | G1 female@ | + | +:/6.4b |

[a, analysis by RIA in 1987;
b, analysis in 1988;
*, 1 iu = 5 μg;
@, daughters of transgenic male 6LL225]

The human FIX protein in transgenic sheep milk has been visualised by Western blotting and also shown to have biological activity. However, the level of protein in the milk is far below that necessary for commercial exploitation.

AATA:

This construct comprises the cDNA encoding human.AAT inserted into the first exon of the BLG gene. It is equivalent to FIXA and thus can be considered as an example of the generalised construct designated pSS1tgXS-TARG as described in W0-A-8800239. It has been used to produce transgenic sheep and mice.

| Sheep | Description | RNA | AAT Protein* |
|---|---|---|---|
| 6LL273 | G0 female | − | − |
| 6LL167 | G0 female | nd | +(2–10 μg/ml) |
| 7LL183 | G0 female | nd | nd |

Figure 14:
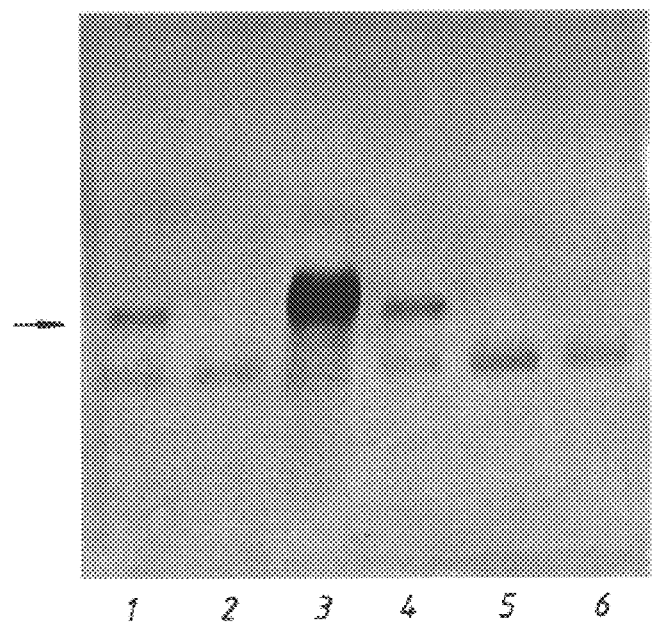
FIG. 14 shows a Western blot of milk whey samples from normal and two transgenic sheep (Example 3)

*protein detected and estimated by Western blotting of milk samples
nd; not done Western blots of milk whey samples from normal and the two transgenic sheep analysed are shown in FIG. 14 [lanes 1, 7LL167(AATA); 2, control sheep whey; 3, human serum pool; 4, 7LL167(AATA); 5, 6LL273(AATA); 6, control sheep whey].

The human AAT (arrowed) is clearly evident in milk whey samples from 6LL167 but is not present in that from 6LL273 or control sheep milk. Under these conditions endogenous AAT present in sheep milk is detected by the anti-human sera and has a greater electrophoretic mobility than its human counterpart.

The levels of human AAT estimated to be present in the transgenic sheep milk are low and are not sufficient for commercial exploitation.

Expression of the AATA construct has also been studied in transgenic mice.

| Mice | Description | RNA | AAT protein* |
|---|---|---|---|
| AATA1.5 | line segregating from AATA1 | – | – |
| AATA1.8 | line segregating from AATA1 | + | +(<<2 μg/ml) |
| AATA5 | mouse-line | + | +(2–10 μg/ml) |
| AATA31 | mouse-line | – | – |

*AAT protein detected and estimated by Western blotting.

Figure 15:
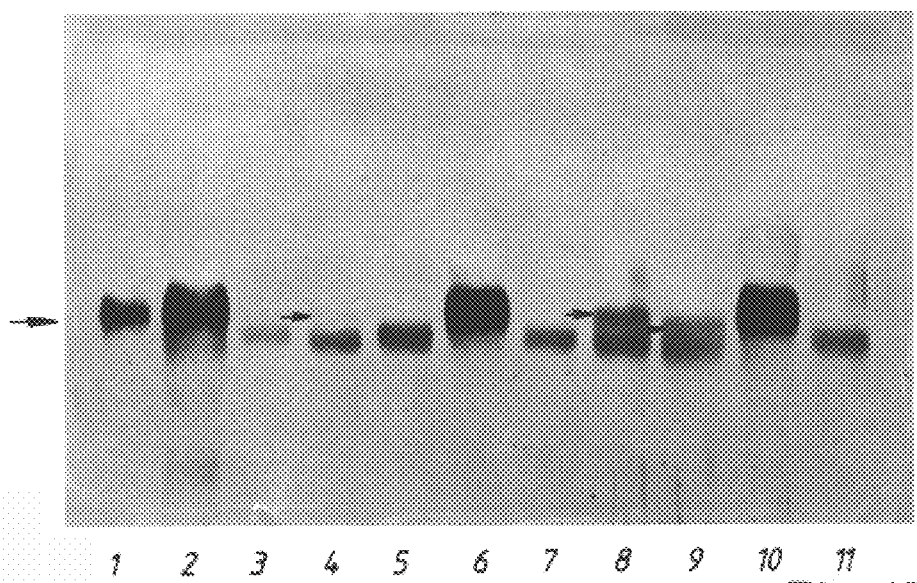
FIG. 15 shows Western blots of TCA-precipitated whey samples from normal and transgenic mice (Example 3)

Western blots of TCA precipitated whey samples from normal and transgenic mice are shown in FIG. 15 [Lanes 1, human alpha$_1$-antitrypsin antigen (Sigma); 2, human serum; 3, mouse serum; 4, AATA 1.8.1 whey; 5, AATA 1.5.10 whey; 6, human and mouse serum; 7, control mouse whey; 8, AATA 5.30 whey; 9, AATA 1 whey; 10, human serum; 11, mouse serum]. The human AAT (arrowed) is clearly evident in preparations from mouse-line AATA5 and is just about visible in mouse-line AATA1.8. Cross-reaction of the anti-human sera with endogenous mouse AAT (which migrates slightly faster than its human counterpart) is also evident.

The levels of expression observed in mouse-line AATA5 are of the same order of magnitude as is observed in transgenic sheep 7LL167, and as such would not prove commercial even if obtained in a dairy animal such as a sheep.

BLG-BLG

This construct comprises the BLG cDNA inserted into exon1 of the BLG structural gene. The construct is analogous to AATA and FIXA (ie pSS1tgXS-TARG) in that the complete structural gene of BLG is present as well as the cDNA insert. In this case, however, the insert is a cDNA encoding a milk protein, rather than a cDNA from a gene normally expressed in another tissue. The expression of this construct was assessed in transgenic mice.

| Mice | Description | RNA | BLG protein* |
|---|---|---|---|
| BB4 | G0 female | + | +(<.005 mg/ml) |
| BB5 | G0 female | + | +(~.005 mg/ml) |
| BB19 | G0 female | + | +(<.005 mg/ml) |
| BB47 | G0 female | + | +(<.005 mg/ml) |
| BB55 | G0 female | nd | +(<.005 mg/ml) |

*detected and estimated by Western blotting
nd = not determined

The construct was expressed tissue-specifically in the four mice in which RNA was analysed. In all five animals low levels of BLG were detected in the milk. These levels of BLG are far below that observed with expression of the normal structural BLG gene (eg see Example 7 in WO-A-8800239). The data show that the 'A-type' construct even when encoding a natural milk protein gene such as BLG (which is known to be capable of very high levels of expression in the mammary gland) is not expressed efficiently in the mammary gland of transgenic mice. This suggests that it may be the configuration of cDNA (whether FIX, AAT or BLG) with the genomic BLG sequence (ie insertion into the first exon) which is responsible for the low levels of expression of this type of construct.

AATD

This construct comprises the AAT cDNA fused to 5' BLG sequences and with 3' sequences from exons 6 and 7 of BLG and the 3' flanking sequences of the BLG gene. This gene contains no introns. Its potential for expression was assessed in transgenic mice:

| Mice | Description | RNA | AAT protein* |
|---|---|---|---|
| AATD12 | G0 female | – | – |
| AATD14 | G0 female | – | – |
| AATD31 | G0 female | – | – |
| AATD33 | G0 female | – | – |
| AATD9 | mouse-line | – | – |
| AAT21 | mouse-line | – | – |
| AATD41 | mouse-line | – | – |
| AATD47 | mouse-line | – | – |

*assessed by Western blotting

None of the transgenic mice carrying AATD expressed the transgene.

FIXD

This is an analogous construct to AATD and comprises the FIX cDNA sequences fused to BLG 5' and 3' sequences (including exons 6 and 7) and contains no introns. Expression was assessed in transgenic mice.

| Mice | Description | RNA | FIX Protein* |
|---|---|---|---|
| FIXD11 | G0 female | – | – |
| FIXD14 | G0 female | – | – |
| FIXD15 | G0 female | – | – |
| FIXD16 | G0 female | – | – |
| FIXD18 | G0 female | – | – |
| FIXD20 | mouse-line | – | – |
| FIXD23 | mouse-line | – | – |
| FIXD24 | mouse-line | – | – |
| FIXD26 | mouse-line | – | – |

*assessed by Western blotting

None of the transgenic mice carrying FIXD expressed the transgene.

These data, together with those from AATD, suggest that a simple configuration of BLG 5' and 3' sequences and target cDNA sequences (ie FIX or AAT) in which no introns are present in the construct will not be expressed efficiently, if at all, in the mammary gland of a transgenic animal.

AATC

This construct comprises the AAT cDNA inserted into the second exon of BLG. It was constructed to determine whether or not inserting the target cDNA (in this case AAT) at a site distant from the promoter (ie in the second rather than in the first exon) would improve the levels of expression. Expression was assessed in transgenic mice.

| Mice | Description | RNA | AAT protein* |
|---|---|---|---|
| AATC14 | G0 female | – | – |
| AATC24 | G0 female | – | – |
| AATC25 | G0 female | – | – |
| AATC30 | G0 female | – | – |
| AATC4 | mouse-line | + | – |
| AATC5 | mouse-line | – | – |
| AATC27 | mouse-line | – | – |

*assessed by Western blotting

Only one out of seven 'lines' expressed the transgene as determined by RNA; in this line no AAT protein was detected, presumably because re-initiation from the initiating ATG of the AAT sequences did not occur. In the RNA-expressing line expression appeared to occur only in the mammary gland although at low levels. These data would suggest that moving the site of insertion of the target cDNA to the second exon (and thus including intron 1 of the BLG) does not yield improved levels of expression of the target cDNA (in this case AAT).

DELTA A2

This construct contains the minimum ovine BLG sequences that have so far been shown in transgenic mice to be required for efficient and tissue-specific expression of BLG in the mammary gland. It is a 5' deletion derivative of pSS1tgXs (WO-A-8800239) and has only 799 bp of sequence flanking the published mRNA cap site (Ali and Clark, (1988) *J. Mol. Biol.* 199, 415–426). This deleted version of pSS1tgXS has been used to produce transgenic mice.

| Mouse | Description | RNA | BLG Protein* |
|---|---|---|---|
| DELTA A2/1 | G0 female | + | +~2 mg/ml |
| DELTA A2/28 | G0 female | + | +~3 mg/ml |
| DELTA A2/38 | G0 female | + | +<0.15 mg/ml |

Detected by Coomassie blue staining: estimated densitometrically.

The DELTA A2 constructs shows that 799 bp of 5' flanking sequences are sufficient for correct and efficient expression of BLG in the mammary gland of transgenic mice. This construct also contains the 4.9 kb transcription unit of BLG and 1.9 kb of 3'flanking sequences. It is conceivable that important regulatory sequences for mammary expression are present in these regions. (However, note the result with AATB in which these sequences were absent and yet efficient mammary expression was obtained.)

EXAMPLE 4

Preparation of Factor IX Construct

Strategy

The expression in transgenic sheep of a human Factor ;IX gene, called BLG-FIX, is disclosed in WO-A-8800239 and Clark et al (1989) (*Biotechnology*, 7 487–492), both of which are herein incorporated by reference, insofar as the law allows. Since this construct has been previously referred to as FIX A, this nomenclature is retained. Essentially the FIX A construct comprises the insertion of a human FIX cDNA into the first intron of the complete (ie all exons and introns present) sheep betalactoglobulin (BLG) gene. This example relates to the modification of this FIX A construct to the effect that the first intron of the human genomic FIX gene has been inserted at the appropriate position, into the FIX cDNA, so that on transcription of the new gene, a primary transcript containing an intron will be produced. When this transcript is correctly spliced, a transcript will be generated, which on translation, will generate exactly the same protein as the original FIX A construct.

The contruction route shown below is complicated, but the methods used are as described in Example 1. The difficulties were caused by the size of human FIX genomic DNA fragments and the requirement to develop new shuttle vectors to allow the suitable manipulation of the BLG and FIX DNA sequences.

Figure 16A:
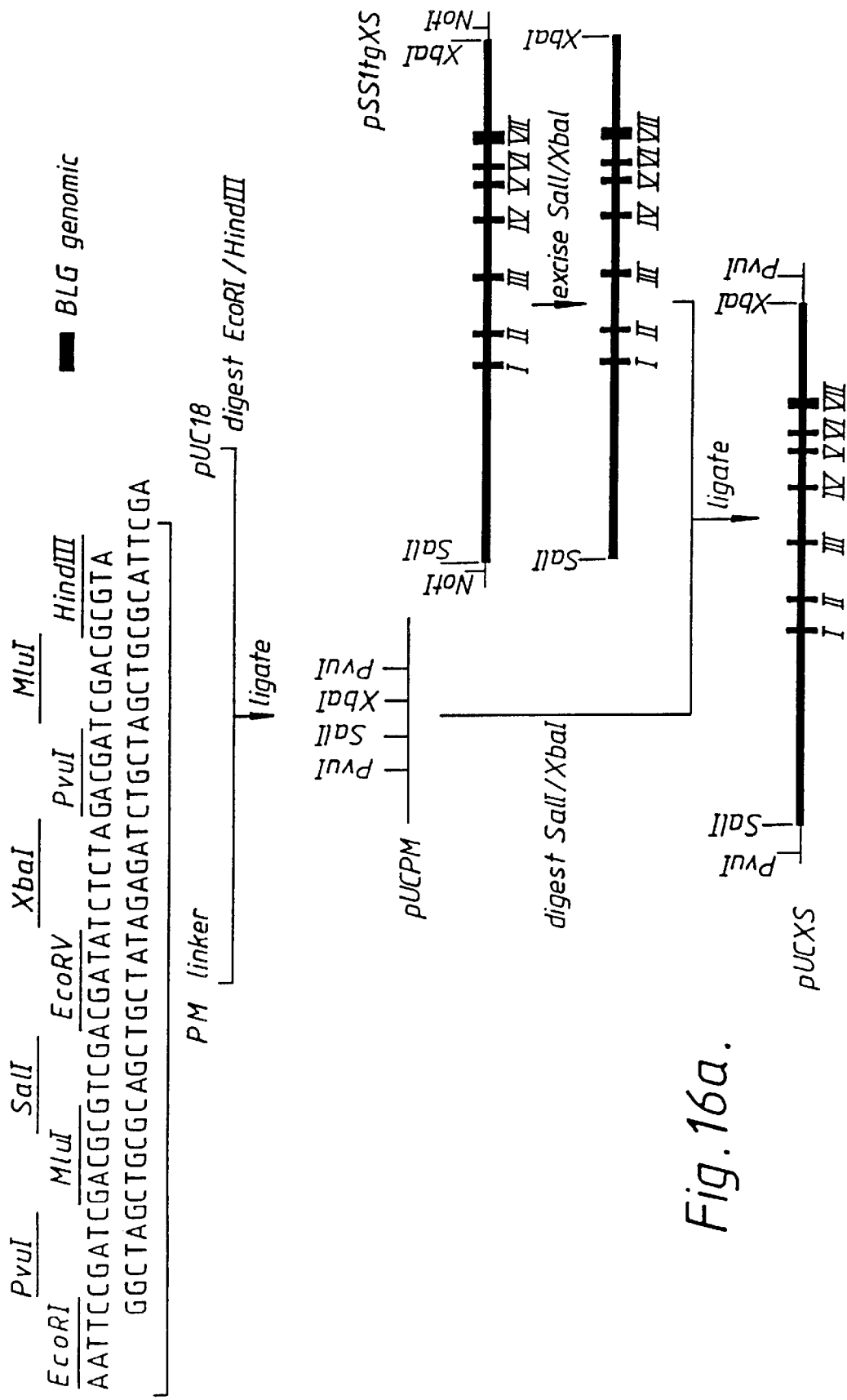
FIGS. 16a, 16b and 17 to 20 show schematically the strategy used for elaborating a further strategy used for elaborating fusion genes comprising DNA sequence elements from ovine beta-lactoglobulin and the gene(s) of interest, in this case Factor IX, to be expressed in the mammary gland of a mammal.
Figure 16B:
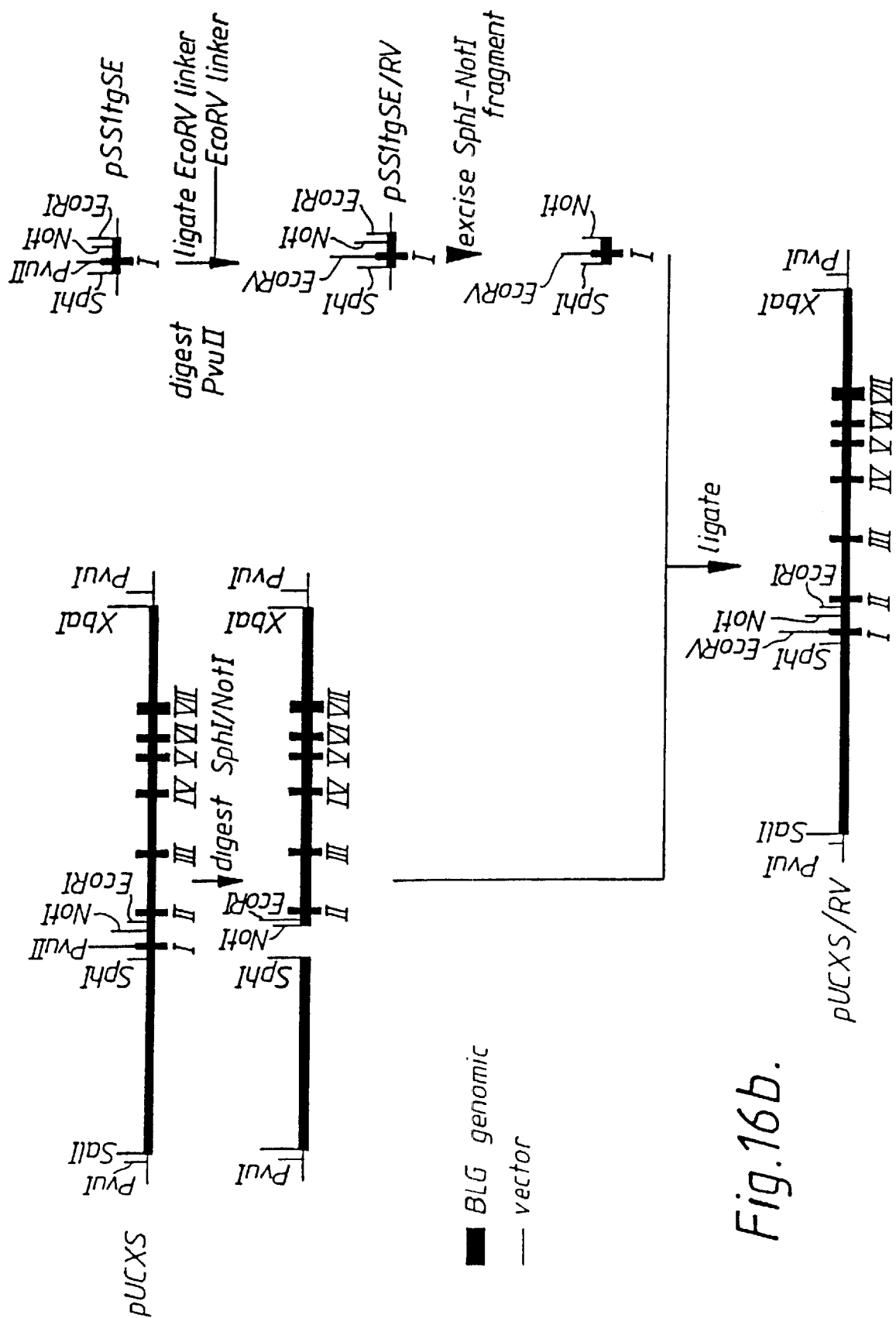
Figure 17:
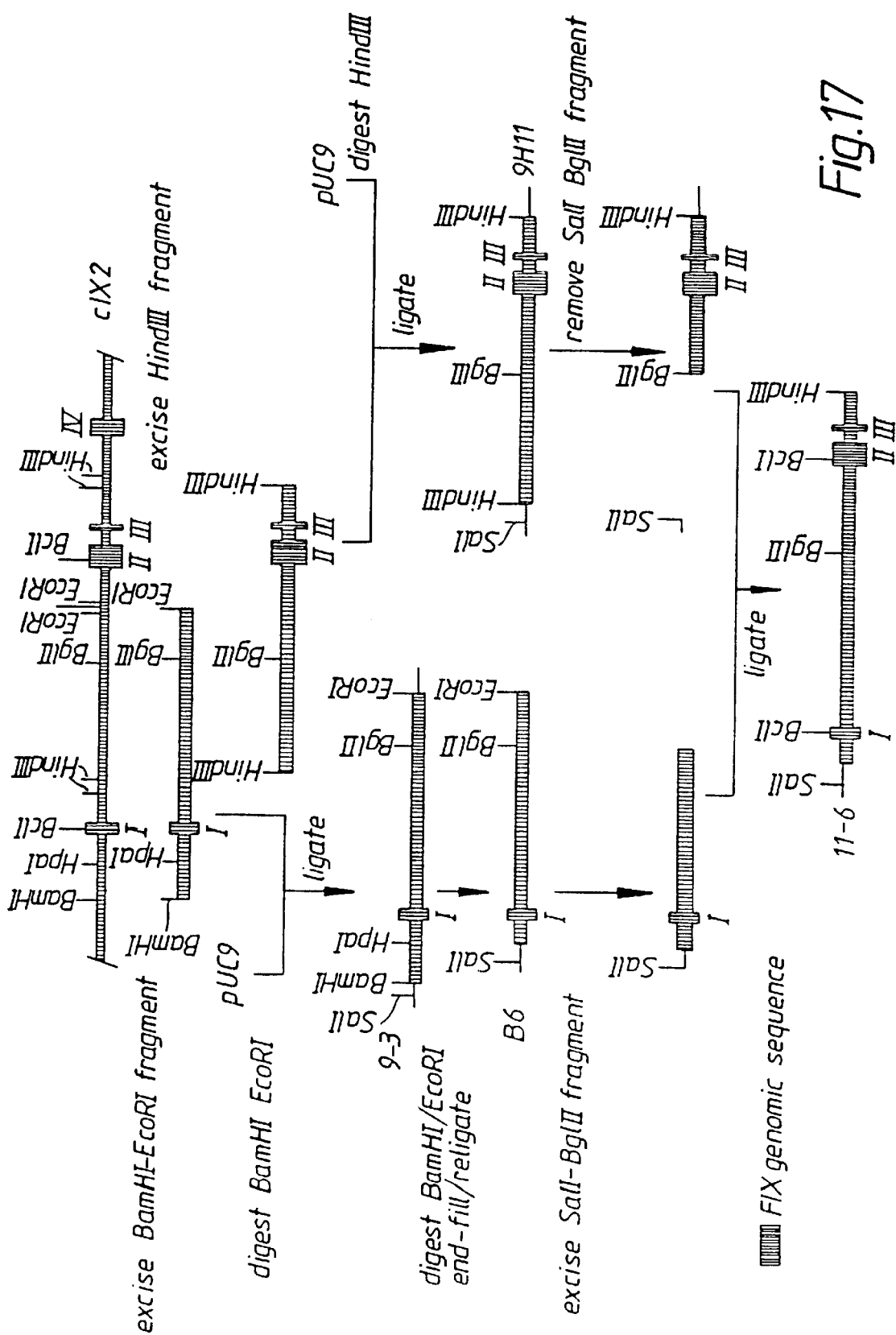

A.
Aims
Construction of
  a) pUC PM—modified cloning vector.
  b) pUC XS—pUC PM containing BLG genomic DNA.
  c) pUC XS/RV—pUC XS containing a unique EcoRV restriction site in the BLG 5' untranslated region.
Details
  i A double stranded synthetic linker DNA including in the following order the restriction sites for the enzymes EcoRI, PvuI, MluI, SalI, EcoRV, XbaI, PvuI, MLuI, HindIII (see FIG. 16a) was ligated into EcoRI/HindIII digested, gel purified, pUc 18 (Boehringer) to generate pUC PM (see FIG. 16a). The insertion was checked by both restriction analysis and direct sequencing.
  ii A SalI-XbaI fragment purified from pSS1tgXS (this contains the XbaI-SalI BLG genomic fragment in pPOLY III.I (see FIG. 3 of WO-A-8800239) was ligated into SalI/XbaI digested, CIP (calf intestinal phosphatase) (see FIG. 16a)—treated, gel purified, pUC PM to give pUC XS. This was checked by restriction analysis.
  iii A synthetic EcoRV linker
      (5' TCGACGCGGCCGCGATATCCATGGATCT)
      (GCTGCGCCGGCGCTATAGGTACCTAGAGATC 5')
      was ligated into the unique PvuLI site of PvuII-digested pSS1tgsE (see WO-A-8800239—pSS1tgSE comprises a SphI-EcoRI fragment of BLG inserted into pPOLY III.I; the PvuII site is 30 bases downstream of cap site in the first exon of BLG)—see FIG. 16b.
  iv The SphI-NotI fragment containing the EcoRV linker was gel purified from pSSItgSE/RV and ligated into the SphI, NotI digested, CIP—treated, gel purified pUC XS, generating pUC XS/RV—see FIG. 16b.
  This was checked by restriction analysis.
B.
Aims
Construction of
  a) Clones 9-3, B6 and 9 H11—cloning vehicles from transfer of various portions of FIX genomic DNA.
  b) Clone 11-6, this comprises exons 1, 2, 3 and introns 1, 2 of FIX inserted into pUC 9.
Details
  i Cosmid clone cIX2, containing part of FIX gene, was obtained from G. Brownlee (see GB-B-2125409, also P. R. Winslip, D. Phil Thesis, Oxford, and Anson et al (1988) *EMBO J.* 7 2795–2799).
  Note In the following description - the assignment of a base number to a restriction site refers to the number of bases the site is upstream (mins sign) or downstream of the cap site in the first FIX exon. These numbers are obtained by analogy, from the published FIX sequence of Yoshitake et al (1985) *Biochemistry* 24 3736–3750.
  ii Clone 9-3 was produced by ligating gel purified BamHI (-2032)–EcoRI (5740) fragment from cIX2 into BamHI/EcoRI-digested, CIP-treated, gel purified, pUC 9 (see FIG. 17).
  iii Clone 9 H11 was made by ligating the gel purified HindIII (810)—HindIII (8329) fragment from cIX2 into HindIII-digested, CIP-treated, gel purified pUC 9 (see FIG. 17).
  iv Clone 9-3 was digested with BamHI and HpaI, end filled with the Klenow enzyme, and the large fragment was gel purified and ligated to produce clone B6 (see FIG. 17). The net effect of this is to remove the FIX sequence between -2032 and -830.

v Clone 9H 11 was digested with SalI and BglII, CIP-treated and then the large fragment, now lacking the regions between the vector SalI site and the FIX BglII site (3996) was gel purified. This was ligated with the gel purified SalI (vector)—BglII (3996) fragment from clone B6, to generate clone 11-6 (see FIG. 17) which contains FIX sequence -830--8329 (ie exons 1,2,3 introns 1,2).

C.
Aims
Construction of
a) Clone C8 (incorporating 5' portion of FIX cDNA).
b) Clone C81.SK (incorporating 5' portion of FIX cDNA+ FIX intron I).

Details i FIX A (FIX cDNA in BLG gene, called BLG FIX in Clark et al, (1989) *Biotechnology* 7 487–492, also see WO-A-8800239) was digested with Sph 1/Bst Y 1. The small fragment was gel purified and ligated into SphI/BamHI-digested, CIP-treated, pUC 18 (Boehringer) generating clone C8 (see FIG. 18) DNA was prepared by growth in a dam⁻ *E. coli* host (SK 383) to allow Bcl digestion.

Figure 18:
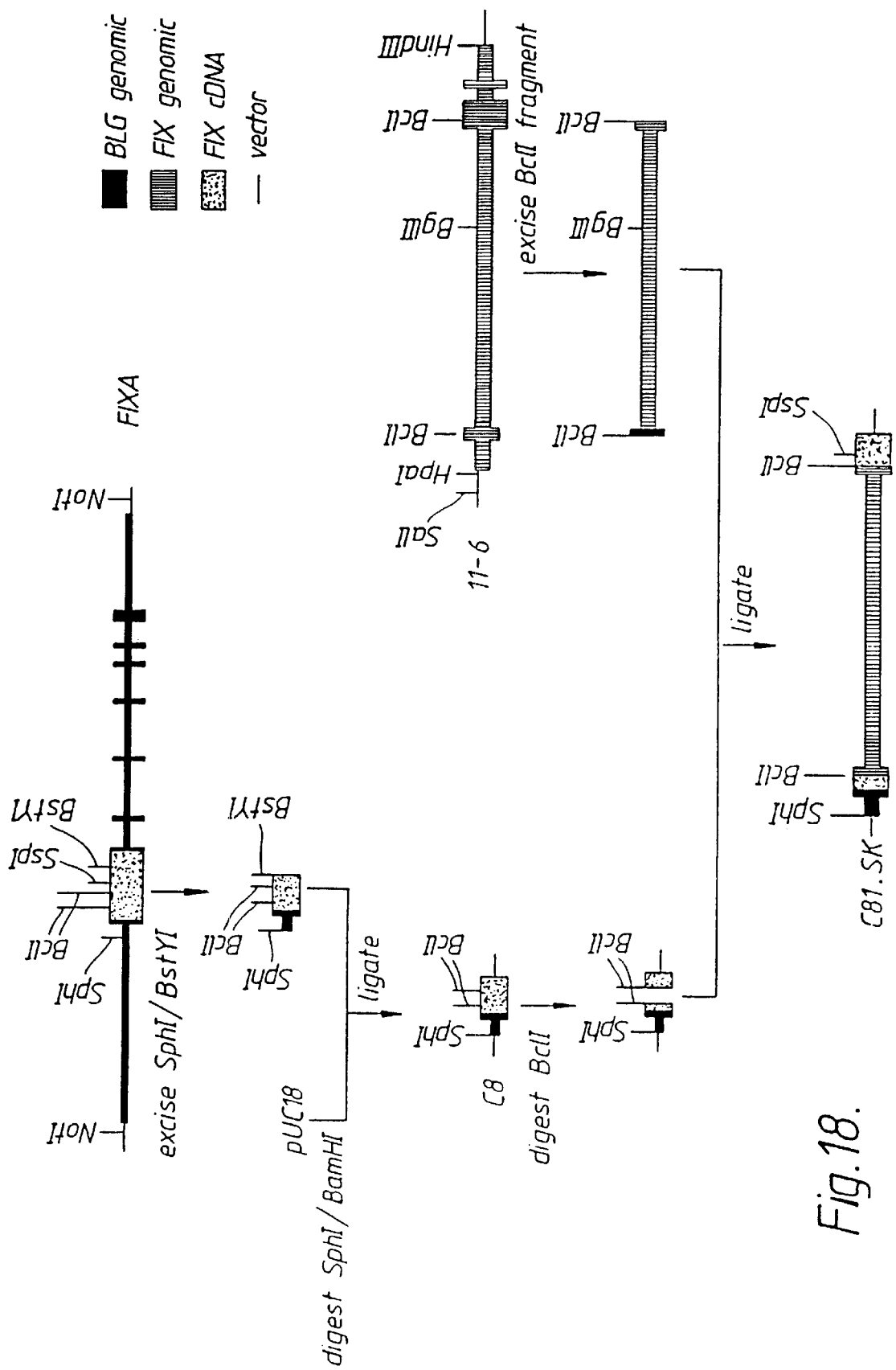

Note C8 contains most of FIX cDNA and 2 out of 3 BclI sites (at positions 2 and 81 upstream of the first nucleotide of the first AUG of the FIX cDNA sequence shown in FIG. 9, GB-B-2125409; these are equivalent to Bcl sites 46 (exon 1) and 6333 (exon 2) of genomic DNA.

ii C8 was digested with BclI, CIP-treated and the large fragment retained after gel purification.

iii Clone 11-6 DNA was prepared from *E. coli* host SK 383 (dam⁻) and the 6287 bp BclI fragment containing intron 1 purified and ligated with the large C8 fragment described in ii above, to generate C81 SK—see FIG. 18. The Bcl junctions were sequenced to confirm reconstruction of Bcl sites.

4.
Aims
Construction of
a) J FIX A (FIX A insert transferred to pUC PM).
b) SP FIX (A cloning vehicle for transfer of intron 1 to J FIX A).

Figure 19:
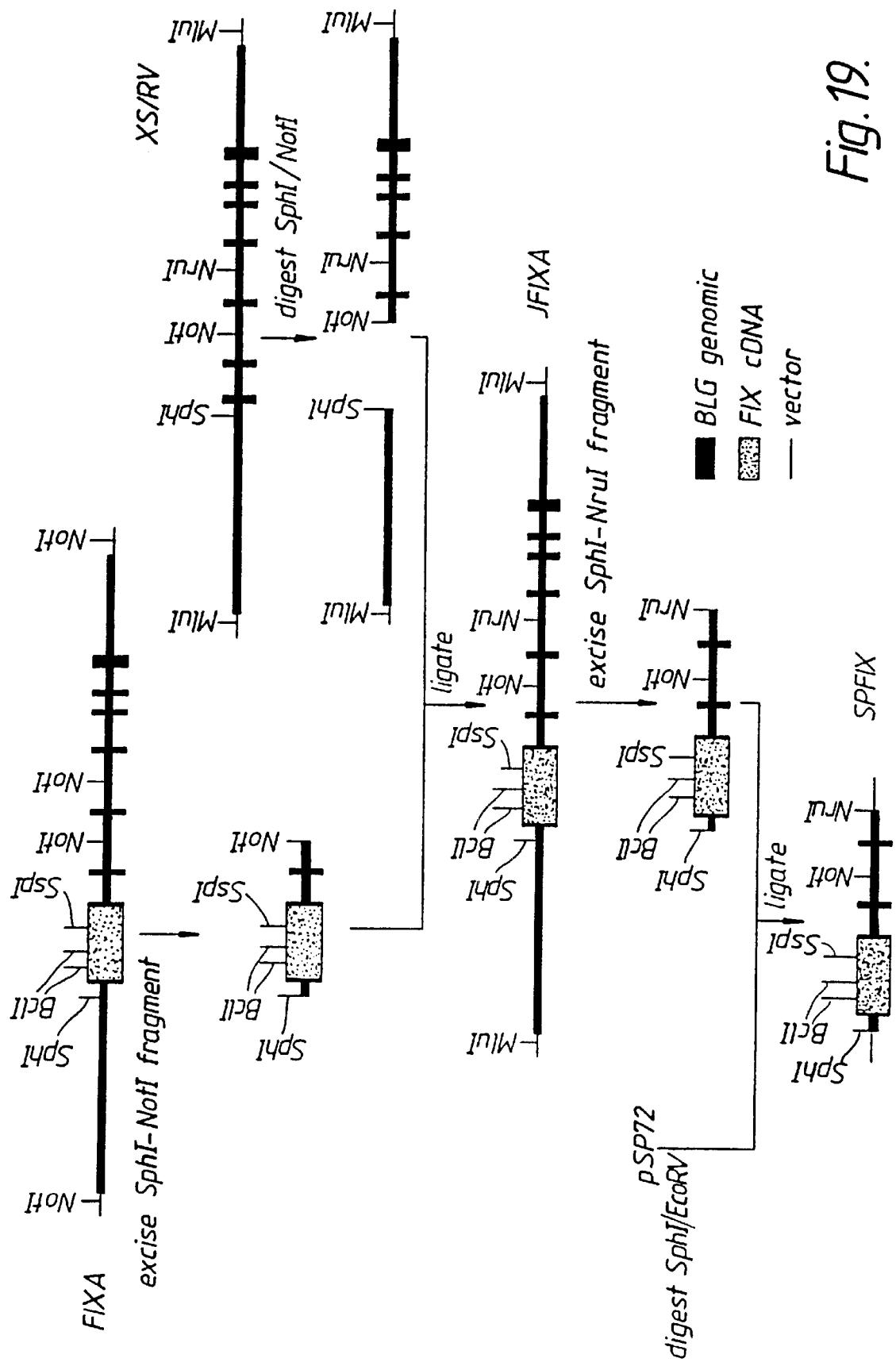

Details i SphI-NotI fragment from FIX A, containing FIX cDNA and flanking BLG sequence was gel purified and ligated into SphI/NotI digested, CIP-treated, gel purified pUC XS/RV to generate J FIX A (see FIG. 19).

ii Sph-NruI fragment containing FIX cDNA from J FIX A was gel purified and ligated into SphI/EcoRV digested, CIP treated, pSP 72 (promega Biotech) to generate SP FIX (see FIG. 19).

E.
Construction of
a) b 11—cloning vehicle containing FIX intron 1.
b) J FIX A 1—final "minigene" construct for construction of trangenics.

Figure 20:
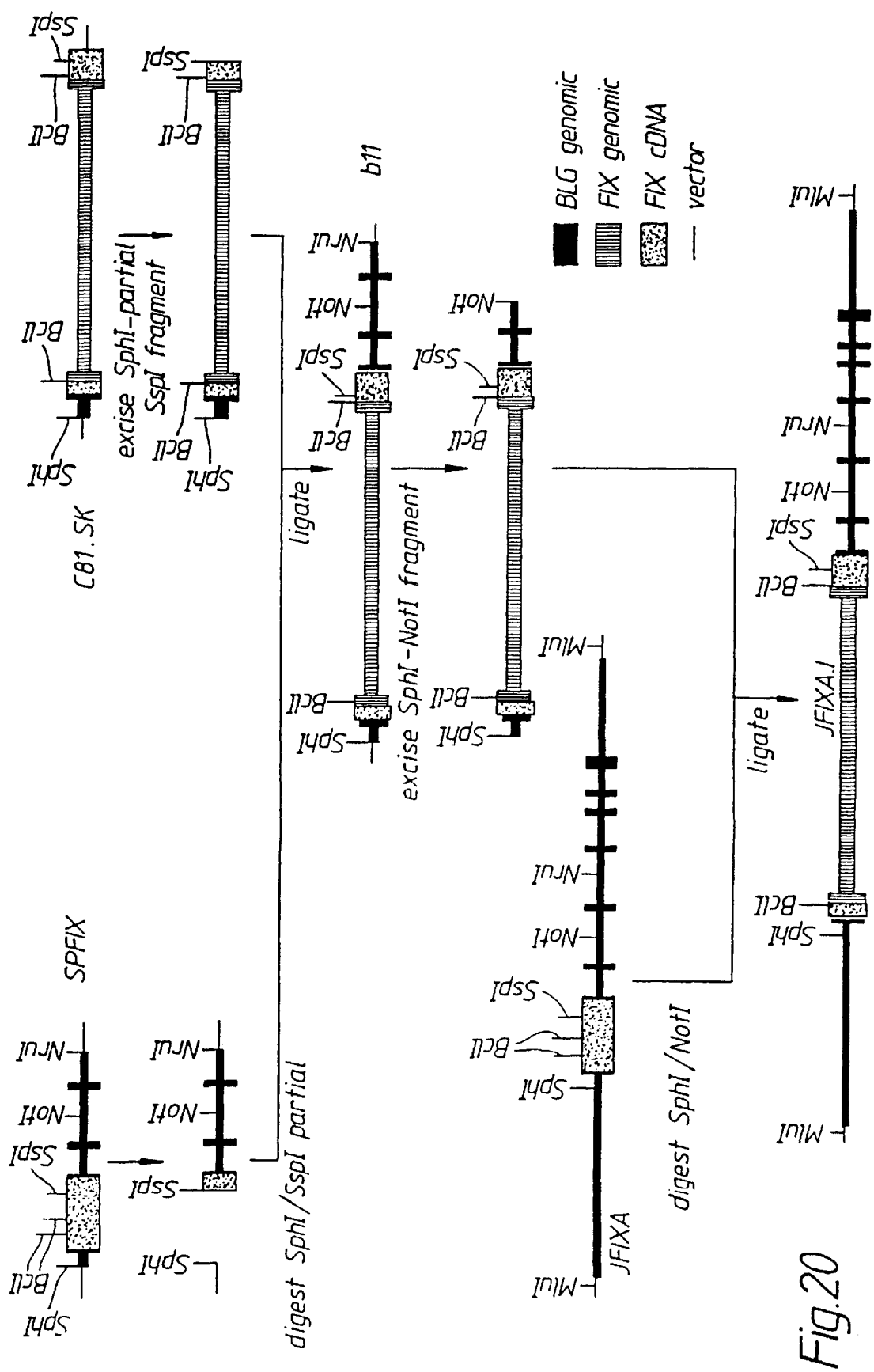

Details i SphI-NotI and C81.SK digested to completion with SphI, then partially digested with Ssp 1*. A 7.2 kb fragment from C81.SK containing FIX intron 1 was ligated with the CIP-treated, gel purified large fragment of SP FIX to generate clone b 11 (see FIG. 20) which contains the complete FIX cDNA and FIX intron 1.

ii The SphI-NotI fragment from b11 containing the FIX sequences was gel purified and ligated into SphI/NotI digested, CIP-treated J FIX A to generate J FIX A 1 (see FIG. 20).

*Note—In SP FIX, there is a SspI site in vector which was not excised in the partially digested fragment shown. Likewise in C81.SK there are four SspI sites in the FIX intron. The 7.2K fragment contains all these four sites and in fact terminates at the SspI site at position 30830 b of the genomic FIX sequence.

F.

Transgenic mice were constructed as described in Example 1B, and identified as described in Example 1C. One male and one female transgenic mice were initially identified.

What is claimed is:

1. A method for producing a heterologous protein, the method comprising expressing said heterologous protein in the milk of a non-human transgenic placental mammal and harvesting the heterologous protein, wherein said non-human transgenic placental mammal has integrated into its genome a genetic construct comprising (a) a 5'-flanking sequence from a mammalian milk protein gene and (b) DNA coding for said heterologous protein other than said milk protein, wherein said DNA comprises at least one whole, but not all, of the introns naturally occurring in the gene coding for said heterologous protein and wherein said 5'-flanking sequence controls expression of said heterologous protein, said genetic construct being integrated into said non-human transgenic placental mammal's genome in such a way that said DNA is expressed in a mammary gland of said mammal at levels greater than those achieved by expression of a corresponding intron-less construct.

2. A method as claimed in claim 1, wherein the transgenic non-human placental mammal transmits the construct to its progeny.

3. A method as claimed in claim 1, wherein the 5'-flanking sequence includes a β-lactoglobulin transcription start site consisting of the SphI-BglII 800 base pair fragment of pSS1tgSpDELTA-AvaII, or any fragment of said SphI-BglII 800 base pair fragment of pSS1tgSpDELTA-AvaII that contains said β-lactoglobulin transcription start site.

4. A method as claimed in claim 1, wherein the 5'-flanking sequence includes a β-lactoglobulin transcription start site consisting of the 4.2 kilobase pair SalI-SphI DNA fragment isolated from the 5'-flanking sequences of the β-lactoglobulin gene or any fragment of said 4.2 kilobase pair SalI-SphI DNA fragment that contains said β-lactoglobulin transcription start site.

5. A method as claimed in claim 1, wherein the milk protein gene is a β-lactoglobulin gene.

6. A method as claimed in claim 1, wherein the heterologous protein is a serine protease inhibitor.

7. A method as claimed in claim 1, wherein the heterologous protein is a blood factor.

8. A method as claimed in claim 1, in which all but one of the natural introns is present in said DNA.

9. A method as claimed in claim 1, in which only one of the natural introns is present in said DNA.

10. A method as claimed in claim 1, in which the construct comprises a 3'flanking region derived from said mammalian milk protein gene or from said DNA coding for said heterologous protein.

* * * * *